US007872021B2

(12) United States Patent
Lebreton et al.

(10) Patent No.: US 7,872,021 B2
(45) Date of Patent: *Jan. 18, 2011

(54) LXR RECEPTOR MODULATORS

(75) Inventors: Luc Lebreton, Dijon (FR); Christine Massardier, Dijon (FR); Christine Dumas, Talant (FR); Pierre Dodey, Fontaine les Dijon (FR); Philippe Masson, Hauteville les Dijon (FR)

(73) Assignee: Laboratories Fournier S.A., Chenove (FR)

( * ) Notice: Subject to any disclaimer, the term of this patent is extended or adjusted under 35 U.S.C. 154(b) by 963 days.

This patent is subject to a terminal disclaimer.

(21) Appl. No.: 11/593,474

(22) Filed: Nov. 7, 2006

(65) Prior Publication Data

US 2007/0099960 A1 May 3, 2007

Related U.S. Application Data

(63) Continuation of application No. PCT/FR2005/001139, filed on May 9, 2005.

(30) Foreign Application Priority Data

May 7, 2004 (FR) .................................. 04 04958

(51) Int. Cl.
*A61K 31/445* (2006.01)
*C07D 211/06* (2006.01)

(52) U.S. Cl. .................... 514/317; 514/183; 514/258.2; 514/231.2; 514/247; 514/252.01; 514/336; 514/423; 544/143; 544/144; 544/224; 544/238; 544/358; 546/201; 546/226; 546/250; 546/255; 548/400; 548/416; 548/452; 548/300.1; 548/532

(58) Field of Classification Search ................. 514/183, 514/228.8, 231.2, 247, 252.01, 252.05, 252.06, 514/252.1, 252.12, 315, 336, 359, 385, 408, 514/410, 412; 544/98, 106, 111, 141, 142, 544/143, 144, 224, 238, 336, 358, 359, 372, 544/373, 376; 546/184, 192, 195, 196, 200, 546/201, 250, 255, 226; 548/400, 416, 452, 548/300.1, 532

See application file for complete search history.

(56) References Cited

U.S. PATENT DOCUMENTS

| | | | | |
|---|---|---|---|---|
| 6,251,932 | B1 * | 6/2001 | Reichelt et al. | 514/414 |
| 6,559,127 | B1 * | 5/2003 | Dappen et al. | 514/19 |
| 7,465,811 | B2 * | 12/2008 | Lebreton et al. | 548/452 |
| 2003/0008861 | A1 | 1/2003 | Lin et al. | |

FOREIGN PATENT DOCUMENTS

| | | | |
|---|---|---|---|
| WO | WO 00/54759 A2 | | 9/2000 |
| WO | WO02005113542 | * | 12/2005 |

OTHER PUBLICATIONS

"Ambinter Screening Library" 2002: 1505846 , XP-002348255, Jan. 1, 2004.
International Search Report dated Oct. 24, 2005 (Eight (8) pages).
* cited by examiner

*Primary Examiner*—Celia Chang
(74) *Attorney, Agent, or Firm*—Crowell & Moring LLP

(57) ABSTRACT

Benzenesulfonamide derivative compounds corresponding to the general formula (I):

(I)

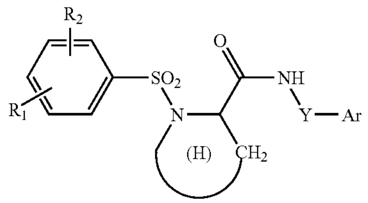

and their pharmaceutically acceptable addition salts; a process for preparation of such compounds; pharmaceutical compositions containing such compounds, and the use of such compounds as a pharmacologically active substance, in particular in the treatment of neurodegenerative diseases, cardiovascular diseases, inflammatory diseases; hypercholesterolemia, and diabetes.

9 Claims, No Drawings

LXR RECEPTOR MODULATORS

CROSS REFERENCE TO RELATED APPLICATIONS

This application is a continuation of international patent application no. PCT/FR2005/001139, filed May 9, 2005, designating the United States of America and published in French on Dec. 22, 2005 as WO 2005/121093, the entire disclosure of which is incorporated herein by reference. Priority is claimed based on French patent application no. FR 04 04958, filed May 7, 2004.

BACKGROUND OF THE INVENTION

The object of this invention is new compounds capable of modulating the activity of nuclear LXR receptors, a method of producing these and pharmaceutical compounds containing them.

Liver X receptors (LXR) are transcription factors belonging to the super family of nuclear receptors to which retinoic acid receptors (RXR), farnesoid X receptors (FXR) and peroxisome proliferator-activated receptors (PPARs) also belong. LXR receptors form, by linking to the RXR receptor, a heterodimer which bonds in a specific manner to the ADN response elements (LXRE) leading to the transactivation of target genes (*Genes dev.* 1995; 9: 1033-45).

These receptors are involved in a number of metabolic routes and are in particular involved in the homeostasis of cholesterol, bile acids, triglycerides and glucose.

Modulation of the activity of these nuclear receptors affects the progression of metabolic disorders such as Type II diabetes, dyslipidemias and the development of atherosclerosis.

The LXR/RXR heterodimer can be activated by LXR and/or RXR ligands. The transactivation of the target genes calls for the recruitment of co-activators such as Grip-1. (*Nature* 1996; 383: 728-31).

The two types of LXR receptors identified today, namely LXRα and LXRβ, have a high degree of similarity in terms of their amino acid sequence but differ in terms of their tissular distribution. LXRα is strongly expressed in the liver and to a lesser extent in the kidneys, the intestine, the adipose tissue and the spleen. LXRβ is distributed in a ubiquitous manner (*Gene* 2000; 243: 93-103, *N.Y. Acad. Sci.* 1995; 761: 38-49).

Although cholesterol does not directly activate the LXR receptors, mono-oxygenated derivatives of cholesterol (oxysterols) do, and more specifically 22(R)-hydroxycholesterol, 24(S)-hydroxycholesterol and 24(S),25-epoxycholesterol. These oxysterols are considered to be the physiological ligands of the LXR receptors (*Nature* 1996; 383: 728-31, *J. Biol. chem* 1997; 272: 3137-40). Furthermore, it has been shown that oxysterol 5,6,24(S),25-diepoxycholesterol is a specific ligand of LXRα, suggesting that it is possible to develop specific ligands of LXRα and/or LXRβ (*Proc. Natl. Acad. Sci USA* 1999; 96: 26-71, *Endocrinology* 2000; 141: 4180-4).

Furthermore, it has been possible to show that human plasma contains natural LXRα and β antagonists (*Steroïds* 2001; 66: 473-479).

Using the hepatocytes of rats, it has been possible to show that unsaturated fatty acids significantly increase the expression of LXRα without affecting LXRβ (*Mol Endocrinol* 2000; 14:161-171). Moreover, the α and γ PPARs activators also induce the expression of LXRα in the human primary macrophages.

The strong concentrations of LXRα in the liver and the identification of the endogenous ligands of LXR have suggested that these receptors play an essential role in cholesterol metabolism. Under physiological conditions, the homeostasis of cholesterol is maintained through regulation of the novo synthesis and catabolism channels. The accumulation of sterols in the liver leads via a feedback mechanism involving transcription factors such as SREBP-1 and SREBP-2 to the inhibition of cholesterol biosynthesis. (*Cell* 1997; 89: 331-40). The excess cholesterol also activates another metabolic route which leads to the conversion of cholesterol into bile acids. The conversion of cholesterol into 7α-hydroxy-cholesterol is performed by a localised enzyme in the liver (CYP7A: 7α-hydroxylase) (*J. Biol. Chem.* 1997; 272: 3137-40).

The involvement of LXR in the synthesis of bile acids and therefore in the regulation of cholesterol homeostasis has been demonstrated using LXRα deficient mice which, when subjected to a fat-rich diet, accumulate large quantities of cholesterol esters at the hepatic level (*Cell* 1998; 93 693-704). The LXRβ deficient mice have the same physiological resistance as the normal mice to a fat-enriched diet. The unchanged expression of the LXRβ in the LXR deficient mice tends to demonstrate that LXRβ is incapable on its own of significantly increasing cholesterol metabolism (*J. Clin. Invest.* 2001; 107: 565-573).

The LXR receptors expressed at the macrophage level play an important role in the regulation of certain functions of this. More specifically, they are involved in control of the inverse transport of cholesterol which allows export of excess cholesterol from the peripheral tissues towards the liver. The cholesterol is taken up by the pre-bHDL via the apoA1 and ABCA1 in order to be transported to the liver where it is catabolised into bile acids and then eliminated.

ABCA1 is a member of the super family of transport proteins (ATP-binding cassette) the importance of which is illustrated by the fact that a mutation at gene level of the ABCA1 is responsible for Tangier disease (*Nat. Genet.* 1999; 22: 336-45).

The expression of ABCA1 and the efflux of cholesterol are induced by the loading of the human macrophages with cholesterol and the activation of the LXR receptors (*Biochem. Biophys. Res. Comm.* 1999; 257: 29-33). It was also subsequently shown that the expression at the intestinal level of ABCG1, ABCG5 and ABCG8, other members of the ABC type transporters family, is also regulated by the RXR/LXR heterodimer (*J. Biol. Chem.* 2000; 275: 14700-14707, *Proc. Natl. Acad. Sci. USA* 2000; 97: 817-22, *J. Biol. Chem.* 2002; 277: 18793-18800, *Proc. Natl. Acad. Sci. USA* 2002; 99: 16237-16242).

It was also shown that LXR agonist ligands reduced atheromatous lesions in two different murine models (ApoE−/− mouse and LDLR−/− mouse) (*Proc. Natl. Acad. Sci. USA* 2002; 99:7604-7609, *FEBS Letters* 2003; 536: 6-11). These results suggest that the LXR ligands can constitute therapeutic agents for treating atherosclerosis.

Finally, it is known that the macrophages play an important role in inflammation in particular in the pathogenesis of atherosclerosis. It has been shown that the activation of the LXRs inhibits the expression of the genes involved in inflammation at the macrophage level. (*Nature Medecine,* 2003; 9: 213-219). In vitro, the expression of mediators, such as nitric oxide synthase, cyclo oxygenase-2(COX-2) and interleukine-6 (IL-6) is inhibited. In vivo, the LXR agonists reduce the inflammation in a dermatite model and inhibit the expression of the genes involved in the inflammation of the aortas of atheromatous mice.

Because cholesterol homeostasis seems also to play an essential role in the operation of the central nervous system and neurodegenerative mechanisms, the ABCA1 expression has also been studied in primary neurone, astrocyte and microglia cultures isolated from the brains of rat embryos. The results of these studies show that LXR activation leads to a reduction in β amyloid secretion and as a consequence to a reduction in amyloid deposits in the brain. This work suggests that LXR activation could represent a new approach to the treatment of Alzheimer's disease (*J. Biol. Chem.* 2003, 275 (15): 13244-13256*, J. Biol. Chem.* 2003, 278 (30): 27688-27694).

LXR receptors are also involved in regulating the expression of apolipoprotein E (ApoE). This protein is heavily involved in the hepatic clearance of lipoproteins and favors the efflux of cholesterol from lipid-rich macrophages. It has been shown that the activation of LXR receptors leads to an increased expression of ApoE via an LXR response element (LXRE) located in the ApoE promoter sequence (*Proc. Natl. Acad. Sci. USA* 2001; 98: 507-512).

Activation of LXR receptors also favored the inverse transport of cholesterol through modulation of the expression of CETP (cholesterol ester transfer protein) which is involved in the transfer of esterified cholesterol from the HDL lipoproteins to the triglyceride-rich lipoproteins eliminated by the liver (*J. Clin. Invest.* 2000; 105: 513-520).

In summary, activation of LXR receptors leads to an increase in the expression of a number of genes favoring the elimination of excess cholesterol from the peripheral tissues. In the cholesterol-loaded macrophage, activation of LXR receptors increases the expression of ABCA1, ABCG1, ABCG5, ABCG8 and ApoE bringing about an increase in the efflux of cholesterol from the macrophages to the liver where it is excreted in the form of bile acids. Induction of CETP and CYP7A expression in the liver leads to an increase in hepatic clearance of cholesterol esters from the HDL lipoproteins and to catabolism of the cholesterol, respectively.

Furthermore, it has also been shown that LXR receptors play an important role in the metabolism of glucose. Treatment of diabetic rodents with an LXR agonist leads to a drastic reduction in plasma glucose levels. In particular, in the insulin resistant Zucker rat (fa/fa), LXR activation inhibits the expression of the genes involved in gluconeogenesis and most particularly of phosphoenolpyruvate carboxykinase (PEPCK) (*J. Biol. Chem.* 2003, 278 (2): 1131-1136). It has also been described how the treatment of mice with an LXR agonist leads to a reduction in plasma glucose levels and in production of hepatic glucose by inhibiting the enzymes that play a key role in gluconeogenesis (*Diabetes,* 53*, suppl* 1, S36-S42 February 2004)

Moreover, it has been shown that an LXR agonist increases glucose tolerance in a murine insulin resistance and obesity model (*Proc. Natl. Acad. Sci. USA* 2003; 100: 5419-5424). The gene expression analysis also highlights regulation of the genes involved in the metabolism of glucose in the liver:

- reduction in peroxisome proliferator-activated receptor coactivator-1α (PGC-1), phosphoenol pyruvate carboxykinase (PEPCK) and glucose-6-phosphatase expression;
- induction of glucokinase expression which favors the use of hepatic glucose.

A transcriptional induction of the insulin-responsive glucose transporter (GLUT4) in the adipose tissue has also been demonstrated. These results underline the importance of LXRs in the coordination of glucose metabolism. It is also known that LXR receptors are involved in the inflammation regulation process (*Nature Medecine* 2003 9, 213-219).

LXR receptor activity modulator compounds are known in the prior art in particular from documents WO 03/090869, WO 03/90746, WO 03/082192 or WO 03/082802; or also from documents WO 03/043985 and WO 04/005253 which describe compounds which are PPAR receptor agonists of the benzenesulfonamide type.

In this context, there is significant interest in finding LXR receptor activity modulator compounds that could be useful in the treatment of certain pathologies such as cardiovascular disease, hypercholesterolemia, dyslipidemia, myocardial infarction, atherosclerosis, diabetes, obesity, inflammation and neurodegenerative diseases.

The present invention is specifically based on the discovery of new LXR receptor activity modulator compounds.

Thus, according to a first aspect, the present invention aims to protect, as a new industrial product, a benzenesulfonamide compound, characterized in that it is chosen from among:

i) the compounds having the formula:

(I)

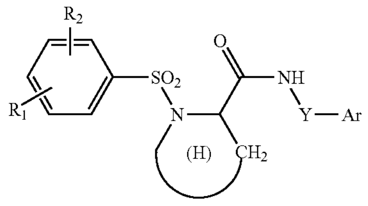

in which (H) represents a nitrogen-containing 5- or 6-membered saturated heterocyclic ring condensed with a phenyl or cyclohexyl ring, optionally substituted by a halogen, a $C_1$-$C_4$ alcoxy group or an $N(R)_2$ group in which R represents the hydrogen atom or a $C_1$-$C_4$ alkyl group, $R_1$ represents:
- a chlorine atom,
- a $C_3$-$C_6$ alkyl group, branched or cyclized,
- a $C_2$-$C_6$ linear, branched or $C_3$-$C_6$ cyclized alkoxy group,
- a phenoxy group, optionally substituted by a halogen,
- a phenyl group, or
- an aminomethyl group, optionally substituted by an acetyl or trifluoroacetyl group, $R_2$ represents a hydrogen atom or a halogen, or, $R_1$ and $R_2$ together form an oxygen-containing or nitrogen-containing heterocycle, optionally substituted by one or more $C_1$-$C_3$ alkyl groups, an acyl group or a $C_2$-$C_3$ perfluoroacyl group, Y represents:
- a single bond,
- a $C_1$-$C_4$, linear or branched or $C_3$-$C_4$ cyclized alkylene group, optionally substituted by a $C_1$-$C_3$ alkoxy group, a phenyl group, an $N(R)_2$ group or a COOH group,
- a $—(CH_2)_n—O—$ group,
- a $—(CH_2)_n—S—$ group, or
- a $—(CH_2)_m—CO—$ group, n is equal to 2 or 3, m is equal to 1, 2 or 3, R represents the hydrogen atom or a $C_1$-$C_4$ alkyl group Ar represents an aromatic or heteroaromatic ring chosen from among the phenyl, naphthalenyl, tetrahydronaphthalenyl, pyridinyl or indolyl groups, optionally substituted by one or two identical or different $R_3$, $R_4$ substituents chosen from among a halogen, a $C_1$-$C_4$ alkyl, $C_1$-$C_4$ alkoxy, nitro, phenyl, phenoxy, trifluoromethyl, amino, hydroxy group, or a group with the formula —X—$[C(R)_2]_p$—$COR_5$ in which:

X represents a single bond, an oxygen atom, a sulfur atom or an NH group, $R_5$ represents OR or $N(R)_2$, R represents the hydrogen atom or a $C_1$-$C_4$ alkyl group, p is equal to 0, 1 or 2;

said substituents $R_3$ and $R_4$ also being able to form together a methylenedioxy group;

ii) the pharmaceutically acceptable salts of the compounds of formula (I).

According to a second aspect, the invention concerns the abovementioned compounds as a pharmacologically active substance. In particular, the invention concerns the use of at least one compound of formula (I) or one of its pharmaceutically acceptable salts as an active substance for the preparation of a medicinal product intended for therapeutic use, in particular for the treatment of hypercholesterolemia, dyslipidemia, diabetes, obesity and cardiovascular disease which are the consequence of an imbalance in the serum lipoproteins. More generally, the compounds of formula I according to the invention are useful for correcting deviations in the parameters indicative of a metabolic syndrome. The compounds according to the invention are also useful as active substances in medicinal products intended for preventing or treating atherosclerosis, myocardial infarction, certain inflammatory diseases such as dermatitis, and neurodegenerative diseases such as Alzheimer's.

DETAILED DESCRIPTION

In the present description, nitrogen-containing 5- or 6-membered saturated heterocyclic ring condensed with a phenyl or cyclohexyl ring, means a heterocycle such as 2,3-dihydroindole, octahydroindole, 1,2,3,4-tetrahydroquinoline, decahydroquinoline, 1,2,3,4-tetrahydroisoquinoline and decahydroisoquinoline. A branched or cyclized $C_3$-$C_6$ alkyl group, means a hydrocarbonated chain having between 3 and 6 carbon atoms, branched or cyclized, for example and without limitation, the groups 1-methylethyl, 1-methylpropyl, 2-methylpropyl, 1,1-dimethylethyl, 1-methylbutyl, 1,1-dimethylpropyl, 1-methylpentyl, 1,1-dimethylbutyl, cyclopropyl, cyclobutyl, cyclopentyl, cyclohexyl or cyclopentylmethyl. A $C_1$-$C_4$ alkyl group means a hydrocarbonated chain having between 1 and 4 carbon atoms, linear or branched, or also cyclical having 3 or 4 carbon atoms. Examples of $C_1$-$C_4$ alkyl groups include the methyl, ethyl, propyl, butyl, 1-methylethyl, 1-methylpropyl, 2-methylpropyl, 1,1-dimethylethyl, cyclopropyl, methylcyclopropyl or cyclopropylmethyl groups. A $C_2$-$C_6$ linear, branched or cyclical alkoxy group means in particular, the ethoxy, propoxy, butoxy, pentyloxy, hexyloxy, 1-methylethoxy, 1-ethylethoxy or cylohexyloxy groups. A linear or branched $C_1$-$C_4$ alkoxy group means in particular the methoxy, ethoxy, propoxy, butoxy, 1-methylethoxy, 1-ethylethoxy, 1- or 2-methylpropoxy groups.

A linear or branched $C_1$-$C_4$ alkylene group means a disubstituted saturated chain comprising between 1 and 4 carbon atoms, for example the —$CH_2$—, —$(CH_2)_2$—, —$(CH_2)_3$—, —$CH(CH_3)$—$CH_2$—, or —$CH_2$—$CH(CH_3)$—$CH_2$— groups.

A halogen means a fluorine, chlorine, bromine or iodine atom, fluorine and chlorine atoms being preferred.

The compounds according to the invention comprise an asymmetrical carbon (carboxamide function carrier) which can be either racemic, or of configuration R or, preferably, of configuration S (Figure Ia)

(Ia)

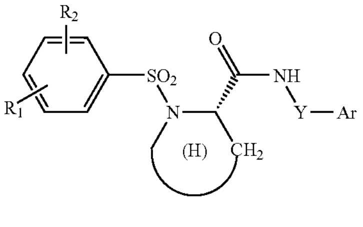

The compounds according to the invention can be prepared using a process that employs the steps of:

a) reacting an acid of formula:

(II)

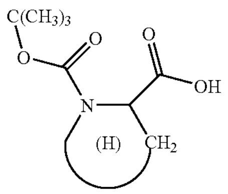

in which (H) represents a nitrogen-containing 5- or 6-membered saturated heterocyclic ring condensed with a phenyl or cyclohexyl ring, optionally substituted by a halogen or a $C_1$-$C_4$ alcoxy group, or an $N(R)_2$ group in which R represents the hydrogen atom or a $C_1$-$C_4$ alkyl group, with an amine of formula $NH_2$—Y—Ar III in which:

Y represents:

a single bond, a linear or branched $C_1$-$C_4$ alkylene, or $C_3$-$C_4$ cyclized group, optionally substituted by a $C_1$-$C_3$ alkoxy group, a phenyl group, an amino group protected by an amino-protecting group (other than Boc) or an $N(R)_2$ group, in which R represents the hydrogen atom or a $C_1$-$C_4$ alkyl group, a —$(CH_2)_n$—O— group, a —$(CH_2)_n$—S— group, or a —$(CH_2)_m$—CO— group, n is equal to 2 or 3, m is equal to 1, 2 or 3, Ar represents an aromatic or heteroaromatic ring chosen from among the phenyl, naphthalenyl, tetrahydronaphthalenyl, pyridinyl or indolyl groups, optionally substituted by one or two substituents $R_3$, $R_4$ that are identical or different and chosen from among a halogen, a $C_1$-$C_4$ alkyl, $C_1$-$C_4$ alkoxy, nitro, phenyl, phenoxy, trifluoromethyl or hydroxy group, an amino group protected by an amino-protecting group (other than Boc), or a group of formula —X—$[C(R)_2]_p$—$COR_5$ in which:

X represents a single bond, an oxygen atom or a sulfur atom $R_5$ represents OH, OR or $N(R)_2$ R represents a $C_1$-$C_4$ alkyl group p is equal to 0, 1 or 2;

said substituents $R_3$ and $R_4$ also being able to form together a methylenedioxy group, in an anhydrous solvent such as dichloromethane and in the presence of a catalyst such as DCC (dicyclohexylcarbodiimide) free or grafted to a resin or HOAT (1-hydroxy-7-azabenzotriazole), at a temperature close to ambient temperature and for between 2 and 20 hours in order to obtain the amide of formula IV

IV

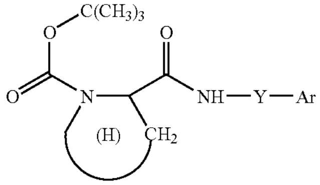

in which (H), Y and Ar retain the same significance as in the starting compounds, b) reacting the resulting compound of formula IV with trifluoroacetic acid, in a solvent such as dichloromethane, at ambient temperature for between 2 and 20 hours in order to obtain the compound of formula V

V

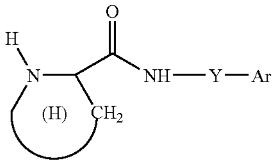

in which (H), Y and Ar retain the same significance as in compound (IV), c) reacting the compound of formula V with a benzenesulfonyl chloride of formula VI

VI

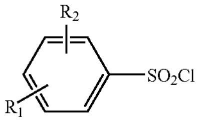

in which $R_1$ represents a chlorine atom, a $C_3$-$C_6$ alkyl group branched or cyclized, a $C_2$-$C_6$ alkoxy group, linear, branched or cyclized, a phenoxy group optionally substituted by a halogen, a phenyl group, an aminomethyl group optionally substituted by an acetyl or trifluoroacetyl group, $R_2$ represents a hydrogen atom or a halogen, or, $R_1$ and $R_2$ together form an oxygen-containing or nitrogen-containing heterocycle, optionally substituted by one or more $C_1$-$C_3$ alkyl groups, by an acyl group or by a $C_2$-$C_3$ perfluoroacyl group in a solvent such as dichloromethane, at ambient temperature for between 2 and 20 hours in order to obtain the compound of formula I

I

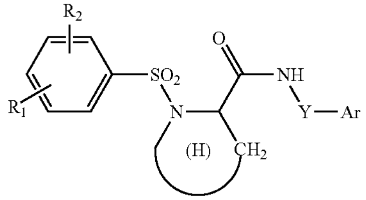

in which $R_1$, $R_2$, (H), Y and Ar retain the same significance as in the starting compounds, d) if necessary, where one of the substituents $R_3$ or $R_4$ of the Ar group represents a protected amino group, eliminating the amino-protecting group to obtain $R_3$ or $R_4$ in the form of a free amine.

As a variant to the process described above, the compounds of formula I according to the invention can be obtained according to a process consisting of a) reacting a benzenesulfonyl chloride of formula VI

VI

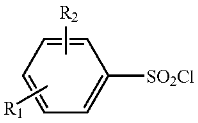

in which $R_1$ represents a chlorine atom, a $C_3$-$C_6$ alkyl group branched or cyclized, a $C_2$-$C_6$ alkoxy group linear, branched or cyclized, a phenoxy group optionally substituted by a halogen, a phenyl group, or an aminomethyl group substituted by an acetyl or trifluoroacetyl group, $R_2$ represents a hydrogen atom or a halogen, or $R_1$ and $R_2$ together form an oxygen-containing or nitrogen-containing heterocycle, optionally substituted by one or more $C_1$-$C_3$ alkyl groups, by an acyl group or by a $C_2$-$C_3$ perfluoroacyl group, with an ester of formula VII

VII

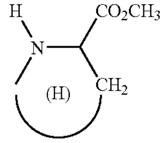

in which (H) represents a nitrogen-containing 5- or 6-membered saturated heterocyclic ring condensed with a phenyl or cyclohexyl ring, optionally substituted by a halogen or a $C_1$-$C_4$ alcoxy group, in an anhydrous solvent such as dichloromethane, at ambient temperature and for between 2 and 10 hours in order to obtain the compound of formula VIII

VIII

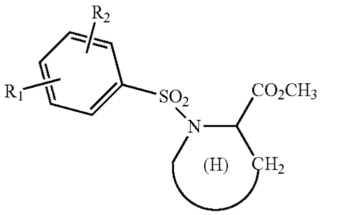

in which (H), $R_1$ and $R_2$ retain the same significance as in the starting compounds, b) converting the ester VIII into acid, through the effect of a base in hydroalcoholic medium according to the methods well known to a person skilled in the art to obtain the acid of formula IX

IX

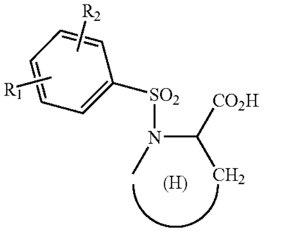

in which (H), $R_1$ and $R_2$ remain unchanged, c) reacting the acid compound (IX) with a primary amine of formula III $NH_2$—Y—Ar III in which Y represents:

a single bond, a $C_1$-$C_4$ alkylene, linear or branched or $C_3$-$C_4$ cyclized group, optionally substituted by a $C_1$-$C_3$ alkoxy group, a phenyl group, an $N(R)_2$ group or a COOH group, a —$(CH_2)_n$—O— group, a —$(CH_2)_n$—S— group, or a —$(CH_2)_m$—CO— group, n is equal to 2 or 3;

m is equal to 1, 2 or 3;

R represents the hydrogen atom or a $C_1$-$C_4$ alkyl group,

Ar represents an aromatic or heteroaromatic ring chosen from among the phenyl, naphthalenyl, tetrahydronaphthalenyl, pyridinyl or indolyl groups, optionally substituted by one or two identical or different $R_3$, $R_4$ substituents chosen from among a halogen, a $C_1$-$C_4$ alkyl, $C_1$-$C_4$ alkoxy, nitro, phenyl, phenoxy, trifluoromethyl, hydroxy or $N(R)_2$ group, an amino group protected by an amino-protecting group, or a group of formula —X—$[C(R)_2]_p$—$COR_5$ in which:

X represents a single bond, an oxygen atom or a sulfur atom, $R_5$ represents OH, OR or $N(R)_2$, R represents a $C_1$-$C_4$ alkyl group, p is equal to 0, 1 or 2;

said substituents $R_3$ and $R_4$ also being capable of forming together a methylenedioxy group, according to a method analogous to that described under step (a) of the above process, in order to obtain the compound of formula (I)

I

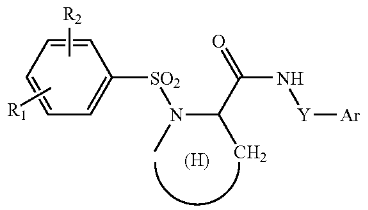

in which (H), $R_1$, $R_2$, Y and Ar retain the same significance as in the starting compounds.

The following examples of the preparation of compounds according to formula (I) will allow a better understanding of the invention. In these examples the term "preparation" is used for examples describing the synthesis of intermediate compounds and the term "examples" for those describing the synthesis of compounds of the formula (I) according to the invention. The melting points are measured on the Kofler test bed and the Nuclear Magnetic Resonance spectral values are characterized by the chemical displacement calculated in relation to the TMS, by the number of protons associated with the signal and by the shape of the signal (s for singlet, d for doublet, dd for double doublet, t for triplet, q for quadruplet, and m for multiplet). The operating frequency and the solvent used are indicated for each compound. The ambient temperature is 20° C.±2° C.

In these examples the following abbreviations have been used:

mmol=millimole

Boc=t-butoxycarbonyl (or: 1,1-dimethylethoxycarbonyl)

HOAT=1-hydroxy-7-azabenzotriazole

Preparation I

1-[[4-(1,1-dimethylethyl)phenyl]sulfonyl]-1,2,3,4-tetrahydro-2-quinolinylcarboxylic acid, methyl ester A solution is prepared of 300 mg (1.32 mmol) of 1,2,3,4-tetrahydro-2-quinolinylcarboxylic acid methyl ester in 20 ml of acetonitrile and, at ambient temperature, 309 mg (1.32 mmol) of 4-(1,1-dimethylethyl)-benzenesulfonyl chloride are added, then 0.29 ml (2.64 mmol) of N-methylmorpholine. The reaction mixture is agitated for 18 hours with solvent reflux and then concentrated under reduced pressure. The evaporation residue is collected in 50 ml of ethyl acetate and washed with a solution of hydrochloric acid 1 N then by a solution of saturated sodium bicarbonate. The organic phase is dried on magnesium sulfate and concentrated under reduced pressure. The raw product is purified by silica gel chromatography eluting with the help of a methylcyclohexane/ethyl acetate mixture (99/1 then 95/5; v/v). In this way the expected product is obtained in the form of a white solid (yield=22%).

NMR $^1H$ (DMSO, 300 MHz) δ: 7.52-7.61 (m, 5H); 7.19-7.24 (m, 1H); 7.05-7.10 (m, 2H); 5.03 (t, 1H); 3.65 (s, 3H);

2.41-2.49 (m, 1H); 2.12-2.17 (m, 1H); 1.89-1.95 (m, 1H); 1.73-1.80 (m, 1H); 1.26 (s, 9H).

Preparation II

1-[[4-(1,1-dimethylethyl)phenyl]sulfonyl]-1,2,3,4-tetrahydro-2-quinolinylcarboxylic acid 112 mg (0.289 mmol) of the compound obtained according to preparation I are mixed with 6 ml of tetrahydrofurane and 4 ml of water and, under agitation and at ambient temperature, 18 mg (0.429 mmol) of lithine are added. This reaction mixture is agitated at ambient temperature for 2 hours, then the acidity is increased to pH 1 by a solution of hydrochloric acid, diluted with water and then extracted by 3 times 25 ml of ethyl acetate. The organic phases collected are dried on magnesium sulfate and concentrated under reduced pressure. In this way the expected product is obtained in the form of an orange solid (yield=86%).

NMR $^1H$ (DMSO, 300 MHz), δ: 7.49-7.74 (m, 6H); 7.16-7.23 (m, 1H); 7.05 (dd, 1H); 4.9 (t, 1H); 2.42-2.51 (m, 1H); 1.80-2.07 (m, 3H); 1.27 (s, 9H).

Example 1

1-[[4-(1,1-dimethylethyl)phenyl]sulfonyl]-N-(2-phenylethyl)-1,2,3,4-tetrahydro-2-quinolinylcarboxamide 150 mg (0.20 mmol) of PS-carbodiimide resin (polystyrene resin functionalised with a carbodiimide group supplied by Argonaut Technologies) are conditioned in 5 ml of dichloromethane for 30 minutes then the solvent is eliminated by filtration. The resin is rinsed by 4 ml of dichloromethane, then 50 mg (0.134 mmol) of the acid obtained according to preparation II in solution in 5 ml of dichloromethane, 25 μl (0.2 mmol) of 2-phenylethanamine and 5 mg of HOAT are added. This reaction mixture is agitated at ambient temperature for 18 hours, and then 200 mg of IR120 resin are added and the reaction mixture is again agitated for 3 hours at ambient temperature. The liquid phase of the mixture is separated by filtration and concentrated under reduced pressure. The raw product is purified by silica gel chromatography eluting using a methylcyclohexane/ethyl acetate mixture (70/30; v/v). In this way the expected product is obtained in the form of a white solid (yield=55%).

Melting point=142-143° C.

NMR $^1H$ (DMSO, 300 MHz) δ: 7.94 (t, 1H); 7.65 (dd, 1H); 7.54 (d, 2H); 7.44 (d, 2H); 7.04-7.24 (m, 8H); 4.66 (t, 1H); 3.29 (m, 2H); 2.66 (t, 2H); 2.27-2.34 (m, 1H); 1.87-1.92 (m, 1H); 1.48-1.66 (m, 2H); 1.26 (s, 9H).

Preparation III

1-[[4-(1,1-dimethylethyl)phenyl]sulfonyl]-2,3-dihydro-(2S)-1H-indole-2-carboxylic acid, methyl ester A solution of 4.25 g (19.9 mmol) of 2,3-dihydro-(2S)-1H-indole-2-carboxylic acid methyl ester hydrochloride in 100 ml of THF (tetrahydrofurane) is prepared and 5.55 ml (39.8 mmol) of triethylamine are added. The mixture is agitated and cooled to 0° C. and a solution of 6.02 g (25.86 mmol) of 4-(1,1-dimethylethyl)benzenesulfonyl chloride in 40 ml of THF is slowly added. The reaction mixture is maintained under agitation for 20 hours at ambient temperature and then hydrolysed with 140 ml of water, and extracted 3 times with 200 ml ethyl acetate. The organic phases collected are washed 3 times with 50 ml of water, then dried on magnesium sulfate and concentrated under reduced pressure. The evaporation residue is purified by silica gel chromatography eluting with the help of a methylcyclohexane/ethyl acetate mixture (90/10 then 80/20; v/v). In this way the expected product is obtained in the form of white crystals (yield=53%).

Melting point=122° C.

NMR $^1H$ (DMSO, 300 MHz) δ: 7.78 (d, 2H, $H_{arom.}$), 7.58 (d, 2H, $H_{arom.}$), 7.38 (d, 1H, $H_{arom.}$), 7.23-7.14 (m, 2H, $H_{arom.}$), 6.99 (t, 1H, $H_{arom.}$), 5.02 (dd, 1H, NCHCO), 3.71 (s, 3H, $OCH_3$), 3.40 (dd, 1H, $CH_2CHCO$), 3.06 (dd, 1H, $CH_2CHCO$), 1.25 (s, 9H, tBu).

Preparation IV

1-[[4-(1,1-dimethylethyl)phenyl]sulfonyl]-2,3-dihydro-(2S)-1H-indole-2-carboxylic acid 2 g (5.36 mmol) of the ester obtained according to preparation III are dissolved in 20 ml of dioxane and 5 ml of water are added, then 0.43 g (10.7 mmol) of sodium hydroxide. The reaction mixture is concentrated under reduced pressure. The white residue is dissolved in 30 ml of water and the solution obtained is acidified by a solution of hydrochloric acid 1M, to pH1. The white precipitate is separated by filtration and then dried in a desiccator. In this way the acid expected is obtained in the form of a white powder (yield=85%).

NMR $^1H$ (DMSO, 300 MHz) δ: 13.10 (s, 1H, COOH), 7.77 (d, 2H, $H_{arom.}$), 7.57 (d, 2H, $H_{arom.}$), 7.36 (d, 1H, $H_{arom.}$), 7.20-7.13 (m, 2H, $H_{arom.}$), 6.98 (t, 1H, $H_{arom.}$), 4.88 (dd, 1H, NCHCO), 3.35 (dd, 1H, $CH_2CHCO$), 3.02 (dd, 1H, $CH_2CHCO$), 1.25 (s, 9H, tBu).

Example 2

1-[[4-(1,1-dimethylethyl)phenyl]sulfonyl]-2,3-dihydro-N-(2-phenoxy-ethyl)-(2S)-1H-indole-2-carboxamide 400 mg (equivalent to 0.556 mmol) of PS-EDC resin (N-(3-dimethylaminopropyl)-N'-ethylcarbodiimide combined with polystyrene resin) are conditioned in 4 ml of dichloromethane under agitation for 15 minutes, and then the solvent is eliminated by filtration. The resin is rinsed several times with 4 ml of dichloromethane, and then a solution of 100 mg (0.278 mmol) of acid obtained according to preparation IV and 25.4 mg (0.185 mmol) of 2-phenoxyethanamine in solution in 6 ml of dichloromethane are added. The mixture is agitated for 20 hours at ambient temperature and 0.278 mmol of isocyanate resin are added. The mixture is agitated for 2 hours at ambient temperature and 0.278 mmol of Amberlite IRA 400 resin are added. The mixture is again agitated for 2 hours and then the resins are eliminated by filtration. The filtrate is then concentrated under reduced pressure. In this way the expected compound is obtained in the form of a white powder (yield=58%).

NMR $^1H$ (DMSO, 250 MHz) δ: 8.37 (t, 1H, NHCO), 7.70 (d, 2H, $H_{arom.}$), 7.55 (d, 2H, $H_{arom.}$), 7.45 (d, 1H, $H_{arom.}$), 7.32-7.20 (m, 3H, $H_{arom.}$), 7.10 (d, 1H, $H_{arom.}$), 7.03-6.93 (m, 4H, $H_{arom.}$), 4.80 (dd, 1H, NCHCO), 4.02 (t, 2H, $CH_2OPh$), 3.50 (m, 2H, $CH_2NCO$), 3.11 (dd, 1H, $CH_2CHCO$), 2.91 (dd, 1H, $CH_2CHCO$), 1.25 (s, 9H, tBu).

Working in a similar way to example 2, the following compounds are obtained:

Example 3

1-[[4-(1,1-dimethylethyl)phenyl]sulfonyl]-2,3-dihydro-N-[2-(4-nitro-phenyl)ethyl]-2S-1H-indole-2-carboxamide Yield=17%; white powder;

NMR $^1$H (DMSO, 300 MHz) δ: 8.22 (t, 1H, NHCO), 8.07 (d, 2H, $H_{arom.}$), 7.66 (d, 2H, $H_{arom.}$), 7.54 (d, 2H, $H_{arom.}$), 7.45 (m, 3H, $H_{arom.}$), 7.22 (t, 1H, $H_{arom.}$), 7.08 (d, 1H, $H_{arom.}$), 7.02 (t, 1H, $H_{arom.}$), 4.68 (dd, 1H, NCHCO), 3.41 (m, 2H, $CH_2NCO$), 2.99 (dd, 1H, $CH_2CHCO$), 2.89 (t, 2H, $CH_2Ph$), 2.79 (dd, 1H, $CH_2CHCO$), 1.24 (s, 9H, tBu).

MS (ESI+) m/z 508 ($MH^+$).

Example 4

1-[[4-(1,1-dimethylethyl)phenyl]sulfonyl]-2,3-dihydro-N-[2-(3-fluoro-phenyl)ethyl]-2S-1H-indole-2-carboxamide Yield=26%; white powder;

NMR $^1$H (DMSO, 300 MHz) δ: 8.22 (t, 1H, NHCO), 7.69 (d, 2H, $H_{arom.}$), 7.55 (d, 2H, $H_{arom.}$), 7.45 (d, 1H, $H_{arom.}$), 7.32-7.20 (m, 2H, $H_{arom.}$), 7.10-6.99 (m, 5H, $H_{arom.}$), 4.69 (dd, 1H, NCHCO), 3.37 (m, 2H, $CH_2NCO$), 3.04 (dd, 1H, $CH_2CHCO$), 2.81 (dd, 1H, $CH_2CHCO$), 2.75 (t, 2H, $CH_2Ph$), 1.25 (s, 9H, tBu);

MS (ESI+) m/z 481 ($MH^+$).

Example 5

1-[[4-(1,1-dimethylethyl)phenyl]sulfonyl]-2,3-dihydro-N-[2-(2,6-dichlorophenyl)ethyl]-2S-1H-indole-2-carboxamide Yield=23%; white powder;

NMR $^1$H (DMSO, 300 MHz) δ: 8.38 (t, 1H, NHCO), 7.69 (d, 2H, $H_{arom.}$), 7.55 (d, 2H, $H_{arom.}$), 7.47-7.40 (m, 3H, $H_{arom.}$), 7.29-7.22 (m, 2H, $H_{arom.}$), 7.10 (d, 1H, $H_{arom.}$), 7.03 (t, 1H, $H_{arom.}$), 4.69 (dd, 1H, NCHCO), 3.33 (m, 2H, $CH_2NCO$), 3.09-3.00 (m, 3H, $CH_2CHCO$, $CH_2Ph$), 2.87 (dd, 1H, $CH_2CHCO$), 1.25 (s, 9H, tBu);

MS (ESI+) m/z 531 ($MH^+$).

Example 6

1-[[4-(1,1-dimethylethyl)phenyl]sulfonyl]-2,3-dihydro-N-(2-phenyl-propyl)-2S-1H-indole-2-carboxamide Yield=15%; colorless oil;

NMR $^1$H (DMSO, 300 MHz), δ: 8.08 (t, 1H, NHCO), 7.69 (d, 2H, $H_{arom.}$), 7.55 (d, 2H, $H_{arom.}$), 7.44 (t, 1H, $H_{arom.}$), 7.30-7.18 (m, 6H, $H_{arom.}$), 7.09 (t, 1H, $H_{arom.}$), 7.01 (td, 1H, $H_{arom.}$), 4.72 (dd, 1H, NCHCO), 3.27 (m, 2H, $CH_2NCO$), 3.05-2.90 (m, 2H, $CH_2CHCO$, CHPh), 2.75 (dd, 1H, $CH_2CHCO$), 1.25 (s, 9H, tBu); 1.18 (d, 3H, $CH_3$).

MS (ESI+) m/z 477 ($MH^+$).

Example 7

1-[[4-(1,1-dimethylethyl)phenyl]sulfonyl]-2,3-dihydro-N-[2-(2-methyl-phenyl)ethyl]-2S-1H-indole-2-carboxamide Yield=19%; colorless oil;

NMR $^1$H (DMSO, 300 MHz), δ:8.17 (t, 1H, NHCO), 7.69 (d, 2H, $H_{arom.}$), 7.55 (d, 2H, $H_{arom.}$), 7.45 (d, 1H, $H_{arom.}$), 7.22-7.10 (m, 3H, $H_{arom.}$), 7.04-6.96 (m, 4H, $H_{arom.}$), 4.71 (dd, 1H, NCHCO), 3.32 (m, 2H, $CH_2NCO$), 3.05 (dd, 1H, $CH_2CHCO$), 2.84 (dd, 1H, $CH_2CHCO$), 2.69 (t, 2H, $CH_2Ph$), 2.27 (s, 3H, $CH_3$), 1.25 (s, 9H, tBu);

MS (ESI+) m/z 477 ($MH^+$).

Example 8

1-[[4-(1,1-dimethylethyl)phenyl]sulfonyl]-2,3-dihydro-N-[2-(3,4-dichlorophenyl)ethyl]-2S-1H-indole-2-carboxamide Yield=18%; colorless oil;

NMR $^1$H (DMSO, 300 MHz), δ: 8.21 (t, 1H, NHCO), 7.69 (d, 2H, $H_{arom.}$), 7.55 (d, 2H, $H_{arom.}$), 7.47 (m, 3H, $H_{arom.}$), 7.22-7.09 (m, 3H, $H_{arom.}$), 7.01 (t, 1H, $H_{arom.}$), 4.68 (dd, 1H, NCHCO), 3.35 (m, 2H, $CH_2NCO$), 3.03 (dd, 1H, $CH_2CHCO$), 2.83-2.78 (m, 3H, $CH_2CHCO$, $CH_2Ph$), 1.25 (s, 9H, tBu);

MS (ESI+) m/z 531 ($MH^+$).

Example 9

1-[[4-(1,1-dimethylethyl)phenyl]sulfonyl]-2,3-dihydro-N-[2-(2-fluoro-phenyl)ethyl]-2S-1H-indole-2-carboxamide Yield=92%; colorless oil;

NMR $^1$H (DMSO, 300 MHz), δ: 8.25 (t, 1H, NHCO), 7.69 (d, 2H, $H_{arom.}$), 7.55 (d, 2H, $H_{arom.}$), 7.45 (d, 1H, $H_{arom.}$), 7.27-7.20 (m, 3H, $H_{arom.}$), 7.15-7.01 (m, 4H, $H_{arom.}$), 4.68 (dd, 1H, NCHCO), 3.35 (m, 2H, $CH_2NCO$), 3.03 (dd, 1H, $CH_2CHCO$), 2.85-2.74 (m, 3H, $CH_2CHCO$, $CH_2Ph$), 1.25 (s, 9H, tBu);

MS (ESI+) m/z 481 ($MH^+$).

Example 10

1-[[4-(1,1-dimethylethyl)phenyl]sulfonyl]-2,3-dihydro-N-[2-(methoxy)-1-(phenylmethyl)ethyl]-2S-1H-indole-2-carboxamide Yield=11%; colorless oil;

NMR $^1$H (DMSO, 300 MHz), δ: 8.01 (d, 1H, NHCO), 7.68 (d, 2H, $H_{arom.}$), 7.55 (d, 2H, $H_{arom.}$), 7.47 (d, 1H, $H_{arom.}$), 7.18-7.03 (m, 8H, $H_{arom.}$), 4.74 (dd, 1H, NCHCO), 4.05 (m, 1H, CHNCO), 3.31 (d, 2H, $OCH_2CHN$), 3.28 (s, 3H, $OCH_3$), 3.02 (dd, 1H, $CH_2CHCO$), 2.78-2.71 (m, 3H, $CH_2CHCO$, $CH_2Ph$), 1.25 (s, 9H, tBu);

MS (ESI+) m/z 507 ($MH^+$).

Example 11

1-[[4-(1,1-dimethylethyl)phenyl]sulfonyl]-2,3-dihydro-N-[E-phenyl-cyclopropyl]-2S-1H-indole-2-carboxamide Yield=24%; white powder;

NMR $^1$H (DMSO, 300 MHz), δ: 8.48 (t, 1H, NHCO), 7.73 (d, 2H, $H_{arom.}$), 7.57 (dd, 2H, $H_{arom.}$), 7.42 (dd, 1H, $H_{arom.}$), 7.26-7.11 (m, 7H, $H_{arom.}$), 7.00 (t, 1H, $H_{arom.}$), 4.67 (dd, 1H, NCHCO), 3.16 (m, 1H, CHNCO), 2.96-2.83 (m, 2H, $CH_2CHCO$), 2.00 (m, 1H, CHPh), 1.25 (s, 9H, tBu), 1.18 (m, 2H, $PhCHCH_2$);

MS (ESI+) m/z 475 ($MH^+$).

Example 12

1-[[4-(1,1-dimethylethyl)phenyl]sulfonyl]-2,3-dihydro-N-(3,3-diphenylpropyl)-2S-1H-indole-2-carboxamide Yield=34%; colorless oil;

NMR $^1H$ (DMSO, 250 MHz), δ: 8.22 (t, 1H, NHCO), 7.72 (d, 2H, $H_{arom.}$), 7.55 (d, 2H, $H_{arom.}$), 7.45 (d, 1H, $H_{arom.}$), 7.29-7.11 (m, 12H, $H_{arom.}$), 7.01 (t, 1H, $H_{arom.}$), 4.71 (dd, 1H, NCHCO), 4.01 (t, 1H; $CH(Ph)_2$), 3.45 (m, 2H, $CH_2NCO$), 3.17-2.86 (m, 2H, $CH_2CHCO$), 2.22 (m, 2H, $CH_2$—CH), 1.25 (s, 9H, tBu).

MS (ESI+) m/z 553 ($MH^+$).

Example 13

1-[[4-(1,1-dimethylethyl)phenyl]sulfonyl]-2,3-dihydro-N-[2-(2-chloro-phenyl)ethyl]-2S-1H-indole-2-carboxamide Yield=31%; white powder;

NMR $^1H$ (DMSO, 300 MHz) δ: 8.26 (t, 1H, NHCO), 7.69 (d, 2H, $H_{arom.}$), 7.55 (d, 2H, $H_{arom.}$), 7.45 (d, 1H, $H_{arom.}$), 7.40 (d, 1H, $H_{arom.}$), 7.25-7.20 (m, 4H, $H_{arom.}$), 7.10 (d, 1H, $H_{arom.}$), 7.03 (t, 1H, $H_{arom.}$), 4.69 (dd, 1H, NCHCO), 3.35 (m, 2H, $CH_2NCO$), 3.03 (dd, 1H, $CH_2CHCO$), 2.89-2.80 (m, 3H, $CH_2CHCO$, $CH_2Ph$), 1.25 (s, 9H, tBu).

MS (ESI+) m/z 497 ($MH^+$).

Example 14

1-[[4-(1,1-dimethylethyl)phenyl]sulfonyl]-2,3-dihydro-N-[2-(3-chloro-phenyl)ethyl]-2S-1H-indole-2-carboxamide Yield=26%; white powder;

NMR $^1H$ (DMSO, 300 MHz) δ: 8.20 (t, 1H, NHCO), 7.70 (d, 2H, $H_{arom.}$), 7.56 (d, 2H, $H_{arom.}$), 7.45 (d, 1H, $H_{arom.}$), 7.29-7.10 (m, 6H, $H_{arom.}$), 7.03 (t, 1H, $H_{arom.}$), 4.69 (dd, 1H, NCHCO), 3.35 (m, 2H, $CH_2NCO$), 3.03 (dd, 1H, $CH_2CHCO$), 2.84-2.72 (m, 3H, $CH_2CHCO$, $CH_2Ph$), 1.25 (s, 9H, tBu);

MS (ESI+) m/z 497 ($MH^+$).

Example 15

1-[[4-(1,1-dimethylethyl)phenyl]sulfonyl]-2,3-dihydro-N-[2-(4-chloro-phenyl)ethyl]-2S-1H-indole-2-carboxamide Yield=24%; white powder;

NMR $^1H$ (DMSO, 300 MHz), δ: 8.17 (t, 1H, NHCO), 7.68 (d, 2H, $H_{arom.}$), 7.55 (d, 2H, $H_{arom.}$), 7.45 (d, 1H, $H_{arom.}$), 7.30-7.18 (m, 5H, $H_{arom.}$), 7.10 (d, 1H, $H_{arom.}$), 7.05 (t, 1H, $H_{arom.}$), 4.69 (dd, 1H, NCHCO), 3.35 (m, 2H, $CH_2NCO$), 3.02 (dd, 1H, $CH_2CHCO$), 2.80 (dd, 1H, $CH_2CHCO$), 2.72 (t, 2H, $CH_2Ph$), 1.25 (s, 9H, tBu).

MS (ESI+) m/z 497 ($MH^+$).

Example 16

1-[[4-(1,1-dimethylethyl)phenyl]sulfonyl]-2,3-dihydro-N-[2-(2,4-dichlorophenyl)ethyl]-2S-1H-indole-2-carboxamide Yield=24%; white powder;

NMR $^1H$ (DMSO, 300 MHz) δ: 8.24 (t, 1H, NHCO), 7.68 (d, 2H, $H_{arom.}$), 7.57-7.54 (m, 3H, $H_{arom.}$), 7.46 (d, 1H, $H_{arom.}$), 7.24 (m, 3H, $H_{arom.}$), 7.11 (d, 1H, $H_{arom.}$), 7.02 (t, 1H, $H_{arom.}$), 4.69 (dd, 1H, NCHCO), 3.34 (m, 2H, $CH_2NCO$), 3.01 (dd, 1H, $CH_2CHCO$), 2.87-2.78 (m, 3H, $CH_2CHCO$, $CH_2Ph$), 1.25 (s, 9H, tBu);

MS (ESI+) m/z 531 ($MH^+$).

Example 17

1-[[4-(1,1-dimethylethyl)phenyl]sulfonyl]-2,3-dihydro-N-(3-phenyl-propyl)-2S-1H-indole-2-carboxamide Yield=19%; white powder;

NMR $^1H$ (DMSO, 300 MHz) δ: 8.20 (t, 1H, NHCO), 7.73 (d, 2H, $H_{arom.}$), 7.57 (d, 2H, $H_{arom.}$), 7.45 (d, 1H, $H_{arom.}$), 7.30-7.11 (m, 7H, $H_{arom.}$), 7.01 (t, 1H, $H_{arom.}$), 4.72 (dd, 1H, NCHCO), 3.16-3.08 (m, 3H, $CH_2NCO$, $CH_2CHCO$), 2.91 (dd, 1H, $CH_2CHCO$), 2.58 (t, 2H, $CH_2Ph$), 1.73 (m, 2H, $CH_2CH_2Ph$) 1.25 (s, 9H, tBu).

MS (ESI+) m/z 477 ($MH^+$).

Example 18

1-[[4-(1,1-dimethylethyl)phenyl]sulfonyl]-2,3-dihydro-N-(4-phenyl-butyl)-2S-1H-indole-2-carboxamide Yield=25%; colorless oil;

NMR $^1H$ (DMSO, 300 MHz) δ: 8.12 (t, 1H, NHCO), 7.71 (d, 2H, $H_{arom.}$), 7.55 (d, 2H, $H_{arom.}$), 7.44 (d, 1H, $H_{arom.}$), 7.29-7.10 (m, 7H, $H_{arom.}$), 7.00 (t, 1H, $H_{arom.}$), 4.71 (dd, 1H, NCHCO), 3.15-3.04 (m, 3H, $CH_2NCO$, $CH_2CHCO$), 2.88 (dd, 1H, $CH_2CHCO$), 2.58 (t, 2H, $CH_2Ph$), 1.60-1.42 (m, 4H, $CH_2CH_2CH_2Ph$), 1.25 (s, 9H, tBu).

MS (ESI+) m/z 491 ($MH^+$).

Example 19

1-[[4-(1,1-dimethylethyl)phenyl]sulfonyl]-2,3-dihydro-N-(phenyl-methyl)-2S-1H-indole-2-carboxamide Yield=42%; white powder;

NMR $^1H$ (DMSO, 300 MHz) δ: 8.72 (t, 1H, NHCO), 7.72 (d, 2H, $H_{arom.}$), 7.55 (d, 2H, $H_{arom.}$), 7.46 (d, 1H, $H_{arom.}$), 7.32-7.22 (m, 6H, $H_{arom.}$), 7.12 (d, 1H, $H_{arom.}$), 7.01 (t, 1H, $H_{arom.}$), 4.82 (dd, 1H, NCHCO), 3.34 (t, 2H, $CH_2NCO$), 3.16 (dd, 1H, $CH_2CHCO$), 2.94 (dd, 1H, $CH_2CHCO$), 1.25 (s, 9H, tBu).

MS (ESI+) m/z 449 ($MH^+$).

Example 20

1-[[4-(1,1-dimethylethyl)phenyl]sulfonyl]-2,3-dihydro-N-[2-(1H-indol-3-yl)ethyl]-2S-1H-indole-2-carboxamide Yield=17%; white powder;

NMR $^1H$ (DMSO, 300 MHz) δ: 8.23 (t, 1H, NHCO), 7.71 (d, 2H, $H_{arom.}$), 7.55 (m, 3H, $H_{arom.}$, NH), 7.46 (d, 1H, $H_{arom.}$), 7.33 (d, 1H, $H_{arom.}$), 7.20 (t, 1H, $H_{arom.}$), 7.14-6.95 (m, 6H, $H_{arom.}$), 4.74 (dd, 1H, NCHCO), 3.38 (m, 2H, $CH_2NCO$), 3.04 (dd, 1H, $CH_2CHCO$), 2.92-2.82 (m, 3H, $CH_2CHCO$, $CH_2Ph$), 1.25 (s, 9H, tBu);

MS (ESI+) m/z 502 ($MH^+$).

Example 21

1-[[4-(1,1-dimethylethyl)phenyl]sulfonyl]-2,3-dihydro-N-[2-(3-pyridinyl)ethyl]-2S-1H-indole-2-carboxamide Yield=25%; white powder;

NMR $^1H$ (DMSO, 300 MHz) δ: 8.42 (m, 2H, $H_{arom.}$), 8.24 (t, 1H, NHCO), 7.69 (d, 2H, $H_{arom.}$), 7.59-7.54 (m, 3H, $H_{arom.}$), 7.45 (d, 1H, $H_{arom.}$), 7.28-7.22 (m, 2H, $H_{arom.}$), 7.10 (d, 1H, $H_{arom.}$), 7.02 (t, 1H, $H_{arom.}$), 4.69 (dd, 1H, NCHCO), 3.38 (m, 2H, $CH_2NCO$), 3.03 (dd, 1H, $CH_2CHCO$), 2.83-2.73 (m, 3H, $CH_2CHCO$, $CH_2Ph$), 1.25 (s, 9H, tBu).

MS (ESI+) m/z 464 ($MH^+$).

Example 22

1-[[4-(1,1-dimethylethyl)phenyl]sulfonyl]-2,3-dihydro-N-(2-oxo-2-phenylethyl)-2S-1H-indole-2-carboxamide Yield=33%; colorless oil;

NMR $^1H$ (DMSO, 300 MHz) δ: 8.46 (t, 1H, NHCO), 7.99 (d, 2H, $H_{arom.}$), 7.72 (d, 2H, $H_{arom.}$), 7.66 (d, 1H, $H_{arom.}$), 7.58-7.46 (m, 5H, $H_{arom.}$), 7.23 (t, 1H, $H_{arom.}$), 7.14 (d, 1H, $H_{arom.}$), 7.03 (t, 1H, $H_{arom.}$), 4.95 (dd, 1H, NCHCO), 4.74 (dd, 1H, $CH_2NCO$), 4.62 (dd, 1H, $CH_2NCO$), 3.15 (dd, 1H, $CH_2CHCO$), 3.01 (dd, 1H, $CH_2CHCO$), 1.25 (s, 9H, tBu).

MS (ESI+) m/z 477 ($MH^+$).

Example 23

1-[[4-(1,1-dimethylethyl)phenyl]sulfonyl]-2,3-dihydro-N-[2-(4-fluoro-phenyl)ethyl]-2S-1H-indole-2-carboxamide Yield=11%; white powder;

NMR 1H (DMSO, 300 MHz) δ: 8.17 (t, 1H, NHCO), 7.68 (d, 2H, $H_{arom.}$), 7.55 (d, 2H, $H_{arom.}$), 7.45 (d, 1H, $H_{arom.}$), 7.22-7.02 (m, 7H, $H_{arom.}$), 4.69 (dd, 1H, NCHCO), 3.35 (m, 2H, $CH_2NCO$), 3.02 (dd, 1H, $CH_2CHCO$), 2.81 (dd, 1H, $CH_2CHCO$), 2.71 (t, 2H, $CH_2Ph$), 1.25 (s, 9H, tBu).

MS (ESI+) m/z 481 ($MH^+$).

Example 24

1-[[4-(1,1-dimethylethyl)phenyl]sulfonyl]-2,3-dihydro-N-[2-(2-pyridinyl)ethyl]-2S-1H-indole-2-carboxamide Yield=20%; white powder;

NMR $^1H$ (DMSO, 300 MHz) δ: 8.49 (dd, 1H, $H_{arom.}$), 8.30 (t, 1H, NHCO), 7.70-7.66 (m, 3H, $H_{arom.}$), 7.55 (d, 2H, $H_{arom.}$), 7.45 (d, 1H, $H_{arom.}$), 7.23-7.19 (m, 3H, $H_{arom.}$), 7.10 (d, 1H, $H_{arom.}$), 7.02 (t, 1H, $H_{arom.}$), 4.71 (dd, 1H, NCHCO), 3.47 (m, 2H, $CH_2NCO$), 3.03 (dd, 1H, $CH_2CHCO$), 2.91-2.82 (m, 3H, $CH_2CHCO$, $CH_2Ph$), 1.25 (s, 9H, tBu).

MS (ESI+) m/z 464 ($MH^+$).

Example 25

1-[[4-(1,1-dimethylethyl)phenyl]sulfonyl]-2,3-dihydro-N-[2-(3,5-dimethoxyphenylethyl]-2S-1H-indole-2-carboxamide Yield=21%; colorless oil;

NMR $^1H$ (DMSO, 300 MHz) δ: 8.17 (t, 1H, NHCO), 7.70 (d, 2H, $H_{arom.}$), 7.55 (d, 2H, $H_{arom.}$), 7.44 (d, 1H, $H_{arom.}$), 7.21 (t, 1H, $H_{arom.}$), 7.10 (d, 1H, $H_{arom.}$), 7.01 (t, 1H, $H_{arom.}$), 6.39 (d, 2H, $H_{arom.}$), 6.33 (t, 1H, $H_{arom.}$), 4.72 (dd, 1H, NCHCO), 3.70 (s, 6H, $OCH_3$), 3.32 (m, 2H, $CH_2NCO$), 3.02 (dd, 1H, $CH_2CHCO$), 2.85 (dd, 1H, $CH_2CHCO$), 2.69 (t, 2H, $CH_2Ph$), 1.25 (s, 9H, tBu);

MS (ESI+) m/z 523 ($MH^+$).

Example 26

1-[[4-(1,1-dimethylethyl)phenyl]sulfonyl]-2,3-dihydro-N-[2-(4-ethylphenyl)ethyl]-2S-1H-indole-2-carboxamide Yield=19%; white powder;

NMR $^1H$ (DMSO, 300 MHz) δ: 8.16 (t, 1H, NHCO), 7.69 (d, 2H, $H_{arom.}$), 7.55 (d, 2H, $H_{arom.}$), 7.45 (d, 1H, $H_{arom.}$), 7.22 (t, 1H, $H_{arom.}$), 7.10 (d, 1H, $H_{arom.}$), 7.09 (s, 4H, $H_{arom.}$), 7.01 (t, 1H, $H_{arom.}$), 4.71 (dd, 1H, NCHCO), 3.31 (m, 2H, $CH_2NCO$), 3.03 (dd, 1H, $CH_2CHCO$), 2.82 (dd, 1H, $CH_2CHCO$), 2.68 (t, 2H, $CH_2Ph$), 2.56 (q, 2H, $CH_2CH_3$), 1.25 (s, 9H, tBu), 1.15 (t, 3H, $CH_3$).

MS (ESI+) m/z 491 ($MH^+$).

Example 27

1-[[4-(1,1-dimethylethyl)phenyl]sulfonyl]-2,3-dihydro-N-[2-(2-phenoxyphenyl)ethyl]-2S-1H-indole-2-carboxamide Yield=11%; colorless oil;

NMR $^1H$ (DMSO, 250 MHz) δ: 8.21 (t, 1H, NHCO), 7.68 (d, 2H, $H_{arom.}$), 7.55 (d, 2H, $H_{arom.}$), 7.45 (d, 1H, $H_{arom.}$), 7.40-6.84 (m, 11H, $H_{arom.}$), 6.84 (t, 1H, $H_{arom.}$), 4.67 (dd, 1H, NCHCO), 3.36 (m, 2H, $CH_2NCO$), 3.02 (dd, 1H, $CH_2CHCO$), 2.86-2.73 (m, 3H, $CH_2CHCO$, $CH_2Ph$), 1.25 (s, 9H, tBu).

MS (ESI+) m/z 555 ($MH^+$).

Example 28

1-[[4-(1,1-dimethylethyl)phenyl]sulfonyl]-2,3-dihydro-N-[(1-naphthalenyl)methyl]-2S-1H-indole-2-carboxamide Yield=13%; white powder;

NMR $^1H$ (DMSO, 250 MHz) δ: 8.73 (t, 1H, NHCO), 8.05 (m, 1H, $H_{arom.}$), 7.94 (m, 1H, $H_{arom.}$), 7.85 (m, 1H, $H_{arom.}$), 7.73 (dd, 2H, $H_{arom.}$), 7.57-7.44 (m, 7H, $H_{arom.}$), 7.22 (t, 1H, $H_{arom.}$), 7.12 (d, 1H, $H_{arom.}$), 7.01 (t, 1H, $H_{arom.}$), 4.92-4.83 (m, 2H, NCHCO, $CH_2NCO$), 4.72 (dd, 1H, $CH_2NCO$), 3.15 (dd, 1H, $CH_2CHCO$), 2.94 (dd, 1H, $CH_2CHCO$), 1.25 (s, 9H, tBu).

MS (ESI+) m/z 499 ($MH^+$).

Example 29

1-[[4-(1,1-dimethylethyl)phenyl]sulfonyl]-2,3-dihydro-N-[2-(4-methyl-phenyl)ethyl]-2S-1H-indole-2-carboxamide Yield=12%; colorless oil;

NMR $^1$H (DMSO, 250 MHz) δ: 8.14 (t, 1H, NHCO), 7.69 (d, 2H, $H_{arom.}$), 7.55 (d, 2H, $H_{arom.}$), 7.45 (d, 1H, $H_{arom.}$), 7.22 (t, 1H, $H_{arom.}$), 7.12-7.01 (m, 6H, $H_{arom.}$), 4.70 (dd, 1H, NCHCO), 3.29 (m, 2H, $CH_2NCO$), 3.03 (dd, 1H, $CH_2CHCO$), 2.83 (dd, 1H, $CH_2CHCO$), 2.67 (t, 2H, $CH_2Ph$), 2.26 (s, 3H, $CH_3$), 1.25 (s, 9H, tBu).

MS (ESI+) m/z 477 ($MH^+$).

Example 30

1-[[4-(1,1-dimethylethyl)phenyl]sulfonyl]-2,3-dihydro-N-(1,2,3,4-tetrahydro-1-naphthalenyl)-2S-1H-indole-2-carboxamide Yield=7%; colorless oil;

NMR $^1$H (DMSO, 250 MHz) δ: 8.52 (t, 1H, NHCO), 7.76 (dd, 2H, $H_{arom.}$), 7.56 (dd, 2H, $H_{arom.}$), 7.41 (dd, 1H, $H_{arom.}$), 7.24-7.12 (m, 6H, $H_{arom.}$), 6.99 (t, 1H, $H_{arom.}$), 4.96 (m, 1H, CHNCO), 4.79 (m, 1H, NCHCO), 3.17 (m, 1H, $CH_2CHCO$), 2.97 (m, 1H, $CH_2CHCO$), 2.76 (m, 2H, $CH_2CH_2CH_2CHNCO$), 1.92-1.69 (m, 4H, $CH_2CH_2CHNCO$), 1.25 (s, 9H, tBu);

MS (ESI+) m/z 489 ($MH^+$).

Example 31

1-[[4-(1,1-dimethylethyl)phenyl]sulfonyl]-2,3-dihydro-N-[2-(2-methoxyphenyl)ethyl]-2S-1H-indole-2-carboxamide Yield=7%; colorless oil;

NMR $^1$H (DMSO, 300 MHz) δ: 8.14 (t, 1H, NHCO), 7.69 (d, 2H, $H_{arom.}$), 7.55 (d, 2H, $H_{arom.}$), 7.45 (d, 1H, $H_{arom.}$), 7.25-6.93 (m, 6H, $H_{arom.}$), 6.84 (t, 1H, $H_{arom.}$), 4.69 (dd, 1H, NCHCO), 3.78 (s, 3H, $OCH_3$), 3.29 (m, 2H, $CH_2NCO$), 3.03 (dd, 1H, $CH_2CHCO$), 2.84 (dd, 1H, $CH_2CHCO$), 2.72 (m, 2H, $CH_2Ph$), 1.25 (s, 9H, tBu).

MS (ESI+) m/z 493 ($MH^+$).

Example 32

1-[[4-(1,1-dimethylethyl)phenyl]sulfonyl]-2,3-dihydro-N-[2-(4-pyridinyl)ethyl]-2S-1H-indole-2-carboxamide Yield=14%; colorless oil;

NMR $^1$H (DMSO, 300 MHz) δ: 8.64 (m, 2H, $H_{arom.}$), 8.29 (t, 1H, NHCO), 7.68-7.63 (m, 4H, $H_{arom.}$), 7.55 (d, 2H, $H_{arom.}$), 7.45 (d, 1H, $H_{arom.}$), 7.23 (t, 1H, $H_{arom.}$), 7.10 (d, 1H, $H_{arom.}$), 7.02 (t, 1H, $H_{arom.}$), 4.66 (dd, 1H, NCHCO), 3.35 (m, 2H, $CH_2NCO$), 3.06-2.94 (m, 3H, $CH_2CHCO$, $CH_2Ph$), 2.80 (dd, 1H, $CH_2CHCO$), 1.25 (s, 9H, tBu).

MS (ESI+) m/z 464 ($MH^+$).

Example 33

1-[[4-(1,1-dimethylethyl)phenyl]sulfonyl]-2,3-dihydro-N-[2-(1,3-benzodioxol-5-yl)ethyl]-2S-1H-indole-2-carboxamide Yield=10%; white powder;

NMR $^1$H (DMSO, 300 MHz) δ: 8.14 (t, 1H, NHCO), 7.70 (d, 2H, $H_{arom.}$), 7.55 (d, 2H, $H_{arom.}$), 7.45 (d, 1H, $H_{arom.}$), 7.22 (t, 1H, $H_{arom.}$), 7.10 (d, 1H, $H_{arom.}$), 7.01 (t, 1H, $H_{arom.}$), 6.78 (m, 2H, $H_{arom.}$), 6.62 (d, 1H, $H_{arom.}$), 5.95 (s, 2H, $OCH_2O$), 4.71 (dd, 1H, NCHCO), 3.26 (m, 2H, $CH_2NCO$), 3.04 (dd, 1H, $CH_2CHCO$), 2.84 (dd, 1H, $CH_2CHCO$), 2.64 (t, 2H, $CH_2Ph$), 1.25 (s, 9H, tBu).

MS (ESI+) m/z 507 ($MH^+$).

Example 34

1-[[4-(1,1-dimethylethyl)phenyl]sulfonyl]-2,3-dihydro-N-[2-(4-phenyl-phenyl)ethyl]-2S-1H-indole-2-carboxamide Yield=11%; white powder;

NMR $^1$H (DMSO, 300 MHz) δ: 8.22 (t, 1H, NHCO), 7.69 (d, 2H, $H_{arom.}$), 7.63 (d, 2H, $H_{arom.}$), 7.55 (d, 4H, $H_{arom.}$), 7.45 (t, 3H, $H_{arom.}$), 7.37-7.22 (m, 4H, $H_{arom.}$), 7.09 (d, 1H, $H_{arom.}$), 7.01 (t, 1H, $H_{arom.}$), 4.74 (dd, 1H, NCHCO), 3.36 (m, 2H, $CH_2NCO$), 3.03 (dd, 1H, $CH_2CHCO$), 2.88-2.75 (m, 3H, $CH_2CHCO$, $CH_2Ph$), 1.25 (s, 9H, tBu).

MS (ESI+) m/z 539 ($MH^+$).

Example 35

1-[[4-(1,1-dimethylethyl)phenyl]sulfonyl]-2,3-dihydro-N-[2-[4-(1,1-dimethylethyl)phenyl]ethyl]-2S-1H-indole-2-carboxamide Yield=10%; white powder;

NMR $^1$H (DMSO, 300 MHz) δ: 8.17 (t, 1H, NHCO), 7.69 (d, 2H, $H_{arom.}$), 7.55 (d, 2H, $H_{arom.}$), 7.45 (d, 1H, $H_{arom.}$), 7.28-7.22 (m, 3H, $H_{arom.}$), 7.10 (d, 3H, $H_{arom.}$), 7.01 (t, 1H, $H_{arom.}$), 4.71 (dd, 1H, NCHCO), 3.31 (m, 2H, $CH_2NCO$), 3.03 (dd, 1H, $CH_2CHCO$), 2.82 (dd, 1H, $CH_2CHCO$), 2.68 (t, 2H, $CH_2Ph$), 1.25 (s, 18H, tBu).

MS (ESI+) m/z 519 ($MH^+$).

Example 36

1-[[4-(1,1-dimethylethyl)phenyl]sulfonyl]-2,3-dihydro-N-[2-(3,4-dimethylphenyl)ethyl]-2S-1H-indole-2-carboxamide Yield=10%; colorless oil;

NMR $^1$H (DMSO, 300 MHz), δ: 8.14 (t, 1H, NHCO), 7.70 (d, 2H, $H_{arom.}$), 7.55 (d, 2H, $H_{arom.}$), 7.45 (d, 1H, $H_{arom.}$), 7.22 (t, 1H, $H_{arom.}$), 7.10 (d, 1H, $H_{arom.}$), 7.03-6.97 (m, 3H, $H_{arom.}$), 6.89 (d, 1H, $H_{arom.}$), 4.71 (dd, 1H, NCHCO), 3.31 (m, 2H, $CH_2NCO$), 3.05 (dd, 1H, $CH_2CHCO$), 2.84 (dd, 1H, $CH_2CHCO$), 2.65 (t, 2H, $CH_2Ph$), 2.18 (s, 6H, $CH_3$), 1.25 (s, 9H, tBu).

MS (ESI+) m/z 491 ($MH^+$).

Example 37

1-[[4-(1,1-dimethylethyl)phenyl]sulfonyl]-2,3-dihydro-N-[2-(2,3-dimethoxyphenyl)ethyl]-2S-1H-indole-2-carboxamide Yield=6%; colorless oil;

NMR $^1$H (DMSO, 300 MHz), δ: 8.22 (t, 1H, NHCO), 7.69 (d, 2H, $H_{arom.}$), 7.55 (d, 2H, $H_{arom.}$), 7.46 (d, 1H, $H_{arom.}$), 7.22 (t, 1H, $H_{arom.}$), 7.10 (d, 1H, $H_{arom.}$), 7.04-6.90 (m, 3H, $H_{arom.}$), 6.70 (d, 1H, $H_{arom.}$), 4.70 (dd, 1H, NCHCO), 3.78 (s, 3H, $OCH_3$), 3.73 (s, 3H, $OCH_3$), 3.29 (m, 2H, $CH_2NCO$), 3.04 (dd, 1H, $CH_2CHCO$), 2.86 (dd, 1H, $CH_2CHCO$), 2.72 (t, 2H, $CH_2Ph$), 1.25 (s, 9H, tBu);

MS (ESI+) m/z 523 ($MH^+$).

Example 38

1-[[4-(1,1-dimethylethyl)phenyl]sulfonyl]-2,3-dihydro-N-[2-(3-methyl-phenyl)ethyl]-2S-1H-indole-2-carboxamide Yield=14%; colorless oil;

NMR $^1H$ (DMSO, 300 MHz), δ: 8.17 (t, 1H, NHCO), 7.70 (d, 2H, $H_{arom.}$), 7.55 (d, 2H, $H_{arom.}$), 7.45 (d, 1H, $H_{arom.}$), 7.22-7.10 (m, 3H, $H_{arom.}$), 7.03-6.98 (m, 4H, $H_{arom.}$), 4.71 (dd, 1H, NCHCO), 3.31 (m, 2H, $CH_2NCO$), 3.05 (dd, 1H, $CH_2CHCO$), 2.84 (dd, 1H, $CH_2CHCO$), 2.69 (t, 2H, $CH_2Ph$), 2.27 (s, 3H, $CH_3$), 1.25 (s, 9H, tBu).

MS (ESI+) m/z 477 ($MH^+$).

Example 39

1-[[4-(1,1-dimethylethyl)phenyl]sulfonyl]-2,3-dihydro-N-[2-[3-(trifluoromethyl)phenyl]ethyl]-2S-1H-indole-2-carboxamide Yield=9%; colorless oil;

NMR $^1H$ (DMSO, 300 MHz), δ: 8.22 (t, 1H, NHCO), 7.69 (d, 2H, $H_{arom.}$), 7.57-7.46 (m, 7H, $H_{arom.}$), 7.22 (t, 1H, $H_{arom.}$), 7.08 (d, 1H, $H_{arom.}$), 7.01 (t, 1H, $H_{arom.}$), 4.69 (dd, 1H, NCHCO), 3.39 (m, 2H, $CH_2NCO$), 3.03 (dd, 1H, $CH_2CHCO$), 2.87-2.75 (m, 3H, $CH_2CHCO$, $CH_2Ph$), 1.25 (s, 9H, tBu).

MS (ESI+) m/z 531 ($MH^+$).

Example 40

1-[[4-(1,1-dimethylethyl)phenyl]sulfonyl]-2,3-dihydro-N-[2-(2,5-dimethoxyphenyl)ethyl]-2S-1H-indole-2-carboxamide 420 mg (0.556 mmol) of PS-carbodiimide resin are conditioned in 4 ml of dichloromethane. After 10 minutes of agitation, the resin is filtered and then rinsed 3 times with 4 ml of dichloromethane. 4 ml of dichloromethane and 4 ml of tetrahydrofurane (THF) are added, and then 100 mg (0.278 mmol) of acid obtained according to preparation IV, 33.5 mg (0.185 mmol) of 2,5-dimethoxybenzeneethanamine and 3.8 mg (0.019 mmol) of HOAT are introduced in succession. The reaction medium is then agitated at ambient temperature. After 16 hours of agitation, 0.278 mmol of IRA400 resin are introduced into the reaction medium and then, after 2 hours of agitation, 0.278 mmol of isocyanate resin. After 1 hour of agitation, the reaction medium is filtered and then the resins are washed 3 times with 3 ml of dichloromethane. The filtrates collected are concentrated and then dried under reduced pressure. In this way the expected compound is obtained in the form of a colorless oil (yield=60%).

NMR $^1H$ (DMSO, 300 MHz) δ: 8.14 (t, 1H, NHCO), 7.69 (d, 2H, $H_{arom.}$), 7.55 (d, 2H, $H_{arom.}$), 7.44 (d, 1H, $H_{arom.}$), 7.21 (t, 1H, $H_{arom.}$), 7.10 (d, 1H, $H_{arom.}$), 7.00 (t, 1H, $H_{arom.}$), 6.87 (d, 1H, $H_{arom.}$), 6.74 (m, 2H, $H_{arom.}$), 4.69 (dd, 1H, NCHCO), 3.73 (s, 3H, $OCH_3$), 3.68 (s, 3H, $OCH_3$), 3.29 (m, 2H, $CH_2NCO$), 3.05 (dd, 1H, $CH_2CHCO$), 2.84 (dd, 1H, $CH_2CHCO$), 2.69 (m, 2H, $CH_2Ph$), 1.25 (s, 9H, tBu).

MS (ESI+) m/z 523 ($MH^+$).

Example 41

1-[[4-(1,1-dimethylethyl)phenyl]sulfonyl]-2,3-dihydro-N-[2-(4-amino-phenyl)ethyl]-2S-1H-indole-2-carboxamide A solution of 100 mg (0,278 mmol) of the acid obtained according to preparation IV is prepared in 4 ml of dichloromethane and 4 ml of THF and then 64 mg (0.334 mmol) of EDCI (1-(3-dimethylaminopropyl)-3-ethylcarbodiimide hydrochloride) and 7.8 mg (0.028 mmol) of HOAT are added. After 10 minutes under agitation at ambient temperature, 45.5 mg (0.334 mmol) of 4-aminobenzeneethanamine are added, as well as 4 ml of dichloromethane/THF mixture (50/50) and 58 μl (0.682 mmol) of triethylamine. The reaction medium is then agitated at ambient temperature for 2 hours. The medium is then treated by the addition of 20 ml of water followed by extraction 3 times with 50 ml of ethyl acetate. The organic phases are then regrouped and washed 3 times with 50 ml of water. The organic phase is then dried on magnesium sulfate, followed by concentration at reduced pressure. The raw product obtained is then purified by silica gel chromatography eluting with the help of a dichloromethane/ethyl acetate mixture (95/5 then 90/10; v/v). In this way the expected product is obtained in the form of a white foam (yield=30%).

NMR $^1H$ (DMSO, 300 MHz) δ: 8.09 (t, 1H, NHCO), 7.68 (d, 2H, $H_{arom.}$), 7.55 (d, 2H, $H_{arom.}$), 7.45 (d, 1H, $H_{arom.}$), 7.22 (t, 1H, $H_{arom.}$), 7.11 (d, 1H, $H_{arom.}$), 7.01 (t, 1H, $H_{arom.}$), 6.82 (d, 2H, $H_{arom.}$), 6.47 (d, 2H, $H_{arom.}$), 4.84 (s, 2H, $PhNH_2$), 4.71 (dd, 1H, NCHCO), 3.23 (m, 2H, $CH_2NCO$), 3.04 (dd, 1H, $CH_2CHCO$), 2.85 (dd, 1H, $CH_2CHCO$), 2.53 (t, 2H, $CH_2Ph$), 1.25 (s, 9H, tBu).

MS (ESI+) m/z 478 ($MH^+$).

Example 42

1-[[4-(1,1-dimethylethyl)phenyl]sulfonyl]-2,3-dihydro-N-[2-(4-hydroxyphenyl)ethyl]-2S-1H-indole-2-carboxamide A solution is prepared of 100 mg (0.278 mmol) of the acid obtained according to preparation IV in 4 ml of dichloromethane and 4 ml of THF and then 64 mg (0.334 mmol) of EDCI (1-(3-dimethylaminopropyl)-3-ethylcarbodiimide hydrochloride) and 7.8 mg (0.028 mmol) of HOAT are added. After 10 minutes under agitation at ambient temperature, 45.8 mg (0.334 mmol) of 4-(2-aminoethyl)phenol are added, along with 4 ml of dichloromethane/THF mixture (50/50) and 58 μl (0.682 mmol) of triethylamine. The reaction medium is then agitated at ambient temperature for 2 hours. The medium is then treated by the addition of 20 ml of water followed by extraction 3 times with 50 ml of ethyl acetate. The organic phases are then regrouped and washed 3 times with 50 ml of water. The organic phase is then dried on magnesium sulfate, then concentrated under reduced pressure. The raw product obtained is then purified by silica gel chromatography eluting with the help of a dichloromethane/ethyl acetate mixture (95/5 then 90/10; v/v). In this way the expected product is obtained in the form of a white solid (yield=40%).

NMR $^1H$ (DMSO, 300 MHz) δ: 9.15 (s, 1H, PhOH), 8.12 (t, 1H, NHCO), 7.69 (d, 2H, $H_{arom.}$), 7.55 (d, 2H, $H_{arom.}$), 7.45 (d, 1H, $H_{arom.}$), 7.22 (t, 1H, $H_{arom.}$), 7.10 (d, 1H, $H_{arom.}$), 7.04-6.95 (m, 3H, $H_{arom.}$), 6.65 (d, 2H, $H_{arom.}$), 4.71 (dd, 1H, NCHCO), 3.25 (m, 2H, $CH_2NCO$), 3.04 (dd, 1H, $CH_2CHCO$), 2.84 (dd, 1H, $CH_2CHCO$), 2.60 (t, 2H, $CH_2Ph$), 1.25 (s, 9H, tBu).

MS (ESI+) m/z 479 ($MH^+$).

Preparation V 2,3-dihydro-2-[[(2-phenylethyl)amino]carbonyl]-(2S)-1H-indole-1-carboxylic acid, 1,1-dimethyl ethyl ester 564 mg (0.75 mmol) of DCC resin (cyclohexylcarbodiimide) are conditioned for 30 minutes at ambient temperature in 8 ml of dichloromethane. The solvent is eliminated by filtration, and then 8 ml of dichloromethane, 132 mg (0.5 mmol) of 2,3-dihydro-(2S)1H-indole-1,2-dicarboxylic acid 1-(1,1-dimethylethyl) ester, 10 mg of HOAT, and then 94 μl (0.75 mmol) of 2-phenylethanamine are added. The reaction mixture is agitated for 16 hours at ambient temperature, and then 1 g of IR 120 resin is added. The mixture is again agitated for 3 hours, and then the resins are eliminated by filtration. The filtrate is then agitated for 2 hours in the presence of 1 g of IRA 400 resin. The resin is eliminated by filtration and the filtrate is concentrated under reduced pressure. In this way the expected amide is obtained in the form of a colorless oil (yield=88%).

NMR $^1$H (DMSO, 300 MHz) δ: 8.14 (s, 1H, NHCO), 7.72 (s, 1H, $H_{arom.}$), 7.31-7.12 (m, 7H, $H_{arom.}$), 7.89 (t, 1H, $H_{arom.}$), 4.68 (dd, 1H, NCHCO), 3.44-3.33 (m, 2H, $CH_2CHCO$, $CH_2NCO$), 3.23 (m, 1H, $CH_2NCO$), 2.82-2.71 (m, 3H, $CH_2Ph$, $CH_2CHCO$), 1.42 (s, 9H, tBu).

MS (ESI+) m/z 367 ($MH^+$).

Preparation VI 2,3-dihydro-N-(2-phenylethyl)-(2S)-1H-indole-2-carboxamide

A solution of 4.3 g (11.7 mmol) of ester obtained according to preparation V in 5 ml of dichloromethane is prepared. Then 4 ml of concentrated trifluoroacetic acid are added and the reaction medium is then agitated at ambient temperature for 24 h. The reaction mixture is then concentrated under reduced pressure and is then neutralised to pH 8 by addition of an aqueous solution of sodium bicarbonate at 10%. The solution obtained is then extracted 3 times with 50 ml of ethyl acetate, and then the organic phase is washed 3 times with 50 ml of water and dried on magnesium sulfate, before being concentrated under reduced pressure. The residue obtained is then purified by silica gel chromatography eluting with a toluene/isopropanol mixture (100/5; v/v). In this way the expected compound is obtained in the form of a beige solid (yield=82%).

Melting point=112-116° C.

Example 43

1-[[4-(1-methylethyl)phenyl]sulfonyl]-2,3-dihydro-N-(2-phenylethyl)-2S-1H-indole-2-carboxamide 96 mg (0.38 mmol) of morpholine resin (morpholinomethyl PS-HL 2% resin DVB Novabiochem) are conditioned in 3 ml of dichloromethane. Following elimination of the solvent, 1 ml of acetonitrile, 52.4 mg (0.24 mmol) of 4(1-methylethyl)benzenesulfonyl chloride, 50 mg (0.187 mmol) of the compound obtained according to preparation VI, and then 3 mg (0.19 mmol) of cesium fluoride are added in succession. The reaction medium is then agitated at ambient temperature. After 20 hours of agitation, the resin is filtered and the filtrate is recovered in 3 ml of dichloromethane and treated with 92 mg (0.24 mmol) of polyamine resin (polyamine resin HL Novabiochem). After 20 hours of agitation, the resin is filtered and the filtrate is recovered in 3 ml of dichloromethane and treated with 0.37 mmol of IR120 Amberlite resin. After 20 hours of agitation, the resin is filtered and the filtrate is concentrated and then dried under reduced pressure. In this way the expected product is obtained in the form of a white solid (yield=45%).

NMR $^1$H (DMSO, 300 MHz) δ: 8.17 (t, 1H, NHCO), 7.68 (d, 2H, $H_{arom.}$), 7.47-7.40 (m, 3H, $H_{arom.}$), 7.27-7.17 (m, 6H, $H_{arom.}$), 7.10 (d, 1H, $H_{arom.}$), 7.01 (t, 1H, $H_{arom.}$), 4.71 (dd, 1H, NCHCO), 3.34 (m, 2H, $CH_2NCO$), 3.02-2.91 (m, 2H, $CH_2CHCO$, $CH(CH_3)_2$), 2.82 (dd, 1H, $CH_2CHCO$), 2.73 (t, 2H, $CH_2Ph$), 1.16 (d, 6H, $CH(CH_3)_2$).

MS (ESI+) m/z 449 ($MH^+$).

Working in a manner similar to example 43, the following compounds are obtained:

Example 44

1-[(3,4-dichlorophenyl)sulfonyl]-2,3-dihydro-N-(2-phenylethyl)-2S-1H-indole-2-carboxamide Yield=46%; white solid;

NMR $^1$H (DMSO, 300 MHz) δ: 8.25 (t, 1H, NHCO), 8.02 (d, 1H, $H_{arom.}$), 7.83 (d, 1H, $H_{arom.}$), 7.72 (dd, 1H, $H_{arom.}$), 7.43 (d, 1H, $H_{arom.}$), 7.27-7.14 (m, 7H, $H_{arom.}$), 7.04 (t, 1H, $H_{arom.}$), 4.84 (dd, 1H, NCHCO), 3.36 (m, 2H, $CH_2NCO$), 3.13 (dd, 1H, $CH_2CHCO$), 2.85 (dd, 1H, $CH_2CHCO$), 2.73 (t, 2H, $CH_2Ph$).

Rf=0.8 ($CH_2Cl_2$/AcOEt: 9/1);

MS (ESI+) m/z 475 ($MH^+$).

Example 45

1-[(4-phenylphenyl)sulfonyl]-2,3-dihydro-N-(2-phenylethyl)-2S-1H-indole-2-carboxamide Yield=28%; white solid;

NMR $^1$H (DMSO, 250 MHz) δ: 8.22 (t, 1H, NHCO), 7.84 (s, 4H, $H_{arom.}$), 7.70 (d, 2H, $H_{arom.}$), 7.51-7.45 (m, 4H, $H_{arom.}$), 7.27-7.03 (m, 8H, $H_{arom.}$), 4.79 (dd, 1H, NCHCO), 3.36 (m, 2H, $CH_2NCO$), 3.08 (dd, 1H, $CH_2CHCO$), 2.85 (dd, 1H, $CH_2CHCO$), 2.74 (t, 2H, $CH_2Ph$).

Rf=0.6 ($CH_2Cl_2$/AcOEt: 9/1);

MS (ESI+) m/z 483 ($MH^+$).

Example 46

2,3-dihydro-1-[(4-phenoxyphenyl)sulfonyl]-N-(2-phenylethyl)-(2S)-1H-indole-2-carboxamide NMR $^1$H (DMSO, 250 MHz) δ: 8.16 (t, 1H); 7.75 (d, 2H); 7.42-7.46 (m, 3H); 7.01-7.30 (1m, 3H); 4.71 (dd, 1H); 3.33 (m, 2H); 3.06 (dd, 1H); 2.84 (dd, 1H); 2.72 (t, 2H).

Example 47

1-[(3,4-dihydro-2,2-dimethyl-2H-benzopyran-6-yl)sulfonyl]-2,3-dihydro-N-(2-phenylethyl)-(2S)-1H-indole-2-carboxamide NMR $^1$H (DMSO, 250 MHz) δ: 8.13 (t, 1H); 7.54 (d, 1H); 7.44 (d, 1H); 7.25 (dd, 1H); 7.15-7.25 (m, 6H); 7.12 (d, 1H); 7.02 (td, 1H); 6.76 (d, 1H); 4.68 (dd, 1H); 3.33 (m, 2H); 3.00 (dd, 1H); 2.62-2.83 (dd, 1H); 2.78 (m, 4H); 1.75 (t, 2H); 1.26 (d, 6H).

Example 48

2,3-dihydro-N-(2-phenylethyl)-1-[[1,2,3,4-tetrahydro-2-(trifluoro-acetyl)-7-isoquinolinyl]sulfonyl]-(2S)-1H-indole-2-carboxamide NMR $^1$H (DMSO, 250 MHz) δ: 8.15 (m, 1H); 7.80 (dd, 1H); 7.55 (m, 1H); 7.46 (d, 1H); 7.34 (d, 1H); 7.09-7.32 (m, 7H); 7.01 (td, 1H); 4.65-4.91 (m, 3H); 3.78 (t, 2H); 3.35 (q, 2H); 2.81-3.06 (m, 4H); 2.73 (t, 2H).

Example 49

2,3-dihydro-1-[[4-(1-methylethoxy)phenyl]sulfonyl]-N-(2-phenyl-ethyl)-(2S)-1H-indole-2-carboxamide NMR $^1$H (DMSO, 250 MHz) δ: 8.15 (t, 1H); 7.64 (d, 1H); 7.44 (d, 2H); 7.10-7.26 (m, 7H); 6.98-7.05 (m, 3H); 4.68 (m, 2H); 3.33 (m, 2H); 3.00 (dd, 1H); 2.83 (dd, 1H); 2.72 (t, 2H); 1.24 (d, 6H).

Working in a manner similar to preparation V, the following compounds are obtained:

Preparation VII

Octahydro-2-[[(2-phenylethyl)amino]carbonyl]-(2S)-1H-indole-1-carboxylic, acid 1,1-dimethyl ethyl ester Yield=48%; white solid;

NMR $^1$H (DMSO, 250 MHz) δ: 7.82 (s, 1H, NHCO), 7.32-7.19 (m, 5H, $H_{arom.}$), 3.99 (dd, 1H, NCHCO), 3.64 (m, 1H, $CHNCOO^tBu$), 3.37-3.20 (m, 2H, $CH_2NCO$), 2.72 (t, 2H, $CH_2Ph$), 2.21 (m, 1H, $CHCH_2CHCO$), 1.90-1.11 (m, 19H, $CH_2CH_2CH_2CH_2CHCH_2CHCO$, tBu).

MS (ESI+) m/z 373 ($MH^+$).

Preparation VIII 2,3-dihydro-N-(2-phenylethyl)-(2S)-1H-indole-2-carboxamide, trifluoroacetate A solution is prepared of 182 mg (0.36 mmol) of the compound obtained according to preparation V in 1.5 ml of dichloromethane and 1.5 ml of trifluoroacetic acid are added. The reaction mixture is agitated at ambient temperature for 16 hours and then the dichloromethane is expelled under reduced pressure. The evaporation residue is then recovered in 5 ml of a water-acetonitrile mixture (90/10; v/v) and the solution obtained is lyophilised. In this way the expected compound is obtained in the form of a white solid (yield=93%).

NMR $^1$H (DMSO, 250 MHz) δ: 7.99 (t, 1H, NHCO), 7.30-7.15 (m, 5H, $H_{arom.}$), 7.06-6.97 (m, 2H, $H_{arom.}$), 6.68 (t, 2H, $H_{arom.}$), 4.40 (s, 1H, NHCHCO), 4.24 (dd, 1H, NCHCO), 3.37-3.25 (m, 3H, $CH_2CHCO$, $CH_2NCO$), 2.88 (dd, 1H, $CH_2CHCO$), 2.73 (t, 2H, $CH_2Ph$).

MS (ESI+) m/z 267 ($MH^+$).

Working in a manner similar to preparation VIII, the following compound is obtained:

Preparation IX

Octahydro-N-(2-phenylethyl)-1H-(2S)-indole-2-carboxamide, trifluoro-acetate

Yield=91%; white solid;

NMR 1H (DMSO, 250 MHz), δ: 9.57 (s, 1H, $NH_2^+$), 8.55 (t, 1H, NHCO), 7.91 (m, 1H, $NH_2^+$), 7.33-7.18 (m, 5H, $H_{arom.}$), 4.13 (m, 1H, NCHCO), 3.61-3.48 (m, 2H, $CHNH_2+$, $CH_2NCO$), 3.34 (m, 1H, $CH_2NCO$), 2.79 (td, 2H, $CH_2Ph$), 2.23 (m, 2H, $CHCH_2CHCO$), 1.76-1.23 (m, 9H, $CH_2CH_2CH_2CH_2CHCH_2CHCO$).

MS (ESI+) m/z 273 ($MH^+$).

Example 50

1-[[4-(1,1-dimethylethyl)phenyl]sulfonyl]-2,3-dihydro-N-(2-phenyl-ethyl)-(2S)-1H-indole-2-carboxamide A mixture is prepared of 144 mg (0.39 mmol) of the compound obtained according to preparation VIII and 0.5 g of IRA400 resin in 2 ml of dichloromethane and this mixture is maintained under agitation at ambient temperature for 3 hours. The resin is then eliminated by filtration and the filtrate is added to a suspension of 202 mg (0.787 mmol) of morpholine resin previously conditioned in 3 ml of dichloromethane. 101 mg (0.432 mmol) of 4-(1,1-dimethylethyl)benzenesulfonyl chloride are added and the reaction mixture is agitated at ambient temperature for 16 hours. The resin is eliminated and the filtrate is agitated for 2 hours, at ambient temperature, with 0.5 g (1.3 mmol) of polyamine resin. This resin is then eliminated by filtration and the filtrate is agitated in the presence of 0.5 g of IR120 resin, for 2 hours at ambient temperature. Following separation of the resin, the filtrate is concentrated under reduced pressure and in this way the expected product is obtained in the form of a brown solid (yield=49%).

NMR $^1$H (DMSO, 300 MHz) δ: 7.93 (m, 1H, NHCO), 7.66 (d, 2H, $H_{arom.}$), 7.54 (d, 2H, $H_{arom.}$), 7.43 (d, 1H, $H_{arom.}$), 7.25-6.99 (m, 8H, $H_{arom.}$), 4.70 (dd, 1H, NCHCO), 3.35 (m, 2H, $CH_2NCO$), 3.01 (dd, 1H, $CH_2CHCO$), 2.89 (dd, 1H, $CH_2CHCO$), 2.73 (t, 2H, $CH_2Ph$), 1.24 (s, 9H, tBu).

MS (ESI+) m/z 463 ($MH^+$).

Working in a manner similar to example 50, starting with the compound obtained according to preparation IX, the following compound is obtained:

Example 51

1-[[4-(1,1-dimethylethyl)phenyl]sulfonyl]-octahydro-N-(2-phenyl-ethyl)-2S-1H-indole-2-carboxamide Yield=76%; colorless oil;

NMR $^1$H (DMSO, 300 MHz) δ: 7.82-7.78 (m, 3H, NHCO, $H_{arom.}$), 7.62 (d, 2H, $H_{arom.}$), 7.32-7.20 (m, 5H, $H_{arom.}$), 3.93 (t, 1H, NCHCO), 3.60 (m, 1H, $CHNSO_2$), 3.37 (m, 2H, $CH_2NCO$), 2.75 (t, 2H, $CH_2Ph$), 1.76-1.10 (m, 20H, $CH_2CH_2CH_2CH_2CHCH_2CHCO$, tBu).

MS (ESI+) m/z 469 ($MH^+$).

Example 52

4-[2-[[[(2S)-1-[[4-(1,1-dimethylethyl)phenyl]sulfonyl]-2,3-dihydro-1H-indol-2-yl]carbonyl]amino]ethoxy]benzoic acid, methyl ester Working in a manner similar to example 2, starting with the compound obtained according to preparation IV and 4-(2-aminoethoxy)benzoic acid methyl ester, the expected compound is obtained in the form of a colorless oil. (yield=85%).

NMR $^1$H (DMSO, 300 MHz): δ: 8.40 (t, 1H); 7.90 (d, 2H); 7.70 (d, 2H); 7.55 (d, 2H); 7.44 (d, 1H); 7.21 (t, 1H); 7.15-6.95 (m, 4H); 4.79 (dd, 1H); 4.12 (t, 2H); 3.81 (s, 3H); 3.65-3.35 (m, 2H); 3.11 (dd, 1H); 2.90 (dd.1H); 1.25 (s, 9H).

Example 53

4-[2-[[[(2S)-1-[[4-(1,1-dimethylethyl)phenyl]sulfonyl]-2,3-dihydro-1H-indol-2-yl]carbonyl]amino]ethoxy]benzoic acid Working in a manner similar to preparation II, starting with the compound obtained according to example 52 and following purification by silica gel chromatography eluting with a dichloromethane/ethanol mixture (98/2; v/v), the expected compound is obtained in the form of a white solid (yield=33.5%)

NMR $^1$H (DMSO, 300 MHz) δ: 12.57 (s wide, 1H); 8.40 (t, 1H); 7.88 (d, 2H); 7.71 (d, 2H); 7.55 (d, 2H); 7.44 (d, 1H); 7.21 (t, 1H); 7.10 (d, 1H); 7.05-6.9 (m, 3H); 4.79 (dd, 1H); 4.11 (t, 2H); 3.65-3.35 (m, 2H); 3.11 (dd, 1H); 2.9 (dd, 1H); 1.25 (s, 9H).

Example 54

4-[2-[[[(2S)-1-[[4-(1,1-dimethylethyl)phenyl]sulfonyl]-2,3-dihydro-1H-indol-2-yl]carbonyl]amino] ethoxy]benzeneacetic acid, methyl ester Working in a manner similar to example 2, starting with the compound obtained according to preparation IV and 4-(2-aminoethoxy)benzeneacetic acid methyl ester, the expected compound is obtained in the form of an oil (yield=35%)

NMR $^1$H (DMSO, 300 MHz): δ: 8.37 (t, 1H); 7.71 (d, 2H); 7.55 (d, 2H); 7.44 (d, 1H); 7.25-7.05 (m, 4H); 7.01 (t, 1H); 6.88 (d, 2H); 4.79 (dd, 1H); 4.00 (t, 2H); 3.60 (s, 3H); 3.59 (s, 2H); 3.6-3.3 (m, 2H); 3.10 (dd, 1H); 2.90 (dd, 1H); 1.25 (s, 9H).

Example 55

4-[2-[[[(2S)-1-[[4-(1,1-dimethylethyl)phenyl]sulfonyl]-2,3-dihydro-1H-indol-2-yl]carbonyl]amino] ethoxy]benzeneacetic acid Working in a manner similar to preparation II, starting with the compound obtained according to example 54, the expected compound is obtained in the form of an oil (yield=81%)

NMR $^1$H (DMSO, 300 MHz) δ: 12.20 (s wide, 1H); 8.37 (t, 1H); 7.71 (d, 2H); 7.55 (d, 2H); 7.44 (d, 1H); 7.25-7.05 (m, 4H); 7.01 (t, 1H); 6.88 (d, 2H); 4.80 (dd, 1H); 4.00 (t, 2H); 3.6-3.3 (m, 4H); 3.10 (dd, 1H); 2.90 (dd, 1H); 1.25 (s, 9H).

Preparation X

1-[(3-cyanophenyl)sulfonyl]-2,3-dihydro-N-(2-phenylethyl)-(2S)-1H-indole-2-carboxamide Working in a manner similar to example 43, starting with 3-cyanobenzenesulfonyl chloride, the expected compound is obtained in the form of a beige solid. (yield=88%).

Melting point=50° C.

Preparation XI

1-[[3-(aminomethyl)phenyl]sulfonyl]-2,3-dihydro-N-(2-phenylethyl)-(2S)-1H-indole-2-carboxamide A solution is prepared of 1 g (2.31 mmol) of the compound obtained according to preparation X in 55 ml anhydrous ethanol and 100 mg Raney nickel are added. The mixture is agitated under a hydrogen atmosphere, at ambient temperature and at atmospheric pressure for 8 hours. The catalyst is then eliminated by filtration and the filtrate is concentrated under reduced pressure. The residue obtained is purified by silica gel chromatography eluting with a dichloromethane/methanol/ammonium mixture (95/5/0.5; v/v/v). In this way the expected compound is obtained in the form of beige solid (yield=48%).

NMR $^1$H (DMSO, 300 MHz) δ: 8.16 (t, 1H); 7.76 (s, 1H); 7.42-7.60 (m, 4H); 7.15-7.30 (m, 6H); 7.09 (dd, 1H); 7.02 (td, 1H); 4.76 (dd, 1H); 3.71 (s, 2H); 3.34 (m, 2H); 2.97 (dd, 1H); 2.83 (dd, 1H); 2.73 (t, 2H).

Example 56

2,3-dihydro-N-(2-phenylethyl)-1-[[3-[[(trifluoroacetyl)amino]methyl]phenyl]sulfonyl]-(2S)-1H-indole-2-carboxamide 474 mg (1.1 mmol) of the compound obtained according to preparation XI are dissolved in 7.5 ml of dichloromethane and 300 μl of triethylamine and 185 μl of trifluoroacetic anhydride are added. The reaction mixture is agitated for 15 hours at ambient temperature, and then hydrolysed on 5 ml of water. The organic phase is separated, dried on magnesium sulfate and concentrated under reduced pressure. The raw product is purified by silica gel chromatography eluting with a dichloromethane/ethyl acetate mixture (85/15; v/v). In this way the expected compound is obtained in the form of a white solid (yield=80%).

Melting point=70° C.

NMR $^1$H (DMSO, 300 MHz): δ: 10.00 (s, 1H); 8.18 (t, 1H); 7.75 (s, 1H); 7.63 (dt, 1H); 7.47-7.57 (m, 2H); 7.43 (d, 1H); 7.15-7.28 (m, 6H); 7.09 (dd, 1H); 7.01 (td, 1H), 4.76 (dd, 1H); 4.41 (s, 2H); 3.33 (m, 2H); 2.98 (dd, 1H); 2.84 (dd, 1H); 2.72 (t, 2H).

Example 57

N-[2-(dimethylamino)-2-phenylethyl]-1-[[4-(1,1-dimethylethyl)phenyl]sulfonyl]-2,3-dihydro-(2S)-1H-indole-2-carboxamide A solution of 100 mg (0.278 mmol) of the acid obtained according to preparation IV is prepared in 4 ml of dichloromethane and 59 mg (0.306 mmol) of EDCI (1-(3-dimethylaminopropyl)-3-ethylcarbodiimide hydro-chloride) and 2.8 mg (0.028 mmol) of HOAT are added. After 10 minutes under agitation at ambient temperature, 51 mg (0.31 mmol) of 2-(dimethylamino)-2-phenylethanamine dissolved in 1 ml of dichloromethane are added. The reaction medium is then agitated at ambient temperature for 20 hours. The medium is then treated by addition of 20 ml of water and then extracted 3 times with 50 ml of dichloromethane. The organic phases are then regrouped and washed 3 times with 50 ml of water, then dried on magnesium sulfate and concentrated under reduced pressure. The raw product obtained is then purified by silica gel chromatography eluting with the help of a dichloromethane/ethanol mixture (95/5; v/v). In this way the expected product is obtained in the form of a white foam (yield=55%).

NMR $^1$H (DMSO, 250 MHz) δ: 7.9-7.75 (m, NH); 7.68 (d, 2H); 7.54 (d, 2H); 7.42 (dd, 1H); 7.40-7.15 (m, 6H); 7.15-6.95 (m, 2H); 4.76 (dd, 1H); 3.75-3.25 (m, 3H); 3.05-2.85 (m, 1H); 2.85-2.55 (m, 1H); 2.10 (s, 3H); 2.09 (s, 3H); 1.25 (s, 9H).

Preparation XII

N,N-dimethyl-4-[2-[[(1,1-dimethylethoxy)carbonyl] amino]ethoxy]benzeneacetamide

A solution is prepared of 1.2 g (4.06 mmol) of 4-[2-(Boc-amino)ethoxy]benzeneacetic acid in 4 ml of dichloromethane and then 932 mg (4.87 mmol) of EDCI and 55 mg (0.406 mmol) of HOAT are added. After 10 minutes under agitation at ambient temperature, 400 mg (4.87 mmol) of dimethylamine hydrochloride are added. The reaction medium is then agitated at ambient temperature for 24 hours. The medium is then treated by the addition of 20 ml of water and then extracted 3 times with 50 ml of dichloromethane. The organic phases are then regrouped and washed 3 times with 50 ml of water, then dried on magnesium sulfate, and concentrated under reduced pressure. The raw product obtained is then purified by silica gel chromatography eluting with the help of a dichloromethane/ethanol mixture (95/5; v/v). In this way the expected product is obtained in the form of a colorless oil (yield=46%).

NMR $^1$H (DMSO, 300 MHz) δ: 7.11 (d, 2H); 7.05-6.9 (m, NH); 6.85 (d, 2H); 3.92 (t, 2H); 3.59 (s, 2H); 3.35-3.20 (m, 2H); 2.97 (s, 3H); 2.81 (s, 3H); 1.38 (s, 9H).

Preparation XIII

4-(2-aminoethoxy)-N,N-dimethyl-benzeneacetamide 200 mg (0.62 mmol) of the product obtained according to preparation XII are dissolved in 5 ml of dichloromethane, 940 µl of trifluoroacetic acid are added. Agitation takes place for 1 hour at ambient temperature. The dichloromethane and the trifluoroacetic acid are evaporated, the product is recovered in water, and the aqueous phase obtained is washed with the help of dichloromethane. The aqueous phase is given an alkaline pH through the addition of a saturated solution of sodium bicarbonate. Extraction is performed with dichloromethane, the organic phase is washed with a minimum of water, and then dried on sodium sulfate and concentrated under reduced pressure. The expected product is obtained in the form of a pale yellow solid with a yield of 20%.

NMR $^1$H (DMSO, 250 MHz) δ: 7.11 (d, 2H); 6.85 (d, 2H); 3.88 (t, 2H); 3.59 (s, 2H); 2.97 (s, 3H); 2.85 (t, 2H); 2.81 (s, 3H).

Example 58

N-[2-[4-[2-(dimethylamino)-2-oxoethyl]phenoxy]ethyl]-1-[[4-(1,1-dimethylethyl)phenyl]sulfonyl]-2,3-dihydro-(2S)-1H-indole-2-carboxamide Working in a manner similar to example 57, starting with the acid obtained according to preparation IV and the product obtained according to preparation XIII, the expected compound is obtained in the form of a colorless oil (yield=48%).

NMR $^1$H (DMSO, 250 MHz) δ: 8.37 (t, NH); 7.72 (d, 2H); 7.54 (d, 2H); 7.45 (d, 1H); 7.21 (t, 1H); 7.2-7.1 (m, 3H); 7.00 (t, 1H); 6.88 (d, 2H); 4.80 (dd, 1H); 4.00 (t, 2H); 3.60 (s, 2H); 3.6-3.35 (m, 2H); 3.11 (dd, 1H); 2.98 (s, 3H); 2.91 (dd, 1H); 2.81 (s, 3H); 1.25 (s, 9H).

Preparation XIV

4-methoxy-2,3-dihydro-1H-indole-2-carboxylic acid, methyl ester 119 mg (4.90 mmol) of magnesium chips are added to a solution of 500 mg (2.44 mmol) of 4-methoxy-1H-indole-2-carboxylic acid in 10 ml of methanol. The mixture is agitated for 3 hours in a bath at 10° C. and then for 1 hour at ambient temperature. 20 ml of hydrochloric acid are added at 0° C. and agitation takes place for one hour. Then a solution of ammonia 3N is added until a pH of 10 is reached and extraction takes place 3 times by 50 ml of ethyl acetate. The organic phases are dried on magnesium sulfate, filtered and concentrated under reduced pressure. The evaporation residue is purified by silica column chromatography eluting with the help of a dichloromethane/ethyl acetate mixture (98/2 then 95-5; v/v). The expected product is obtained in the form of a brown oil with a yield of 64%.

NMR $^1$H (DMSO, 250 MHz) δ: 6.91 (t, 1H); 6.24-6.20 (m, 2H); 5.97 (d, 1H); 4.41-4.34 (m; 1H); 3.70 (s, 3H); 3.65 (s, 3H); 3.17 (dd, 1H); 3.01 (dd, 1H).

Preparation XV

1-[[4-(1,1-dimethylethyl)phenyl]sulfonyl]-4-methoxy-2,3-dihydro-1H-indole-2-carboxylic acid, methyl ester Working in a manner similar to example 43, starting with the product obtained according to preparation XIV and with 4-(1,1-dimethylethyl)benzenesulfonyl chloride, the expected compound is obtained in the form of a brown solid (yield=79%).

NMR $^1$H (DMSO, 300 MHz) δ: 7.77 (d, 2H); 7.58 (d, 2H); 7.20 (t, 1H); 7.01 (d, 1H); 6.67 (d, 1H); 5.02 (dd, 1H); 3.72 (s; 6H); 3.26 (dd, 1H); 2.92 (dd, 1H); 1.27 (s, 9H).

Preparation XVI

1-[[4-(1,1-dimethylethyl)phenyl]sulfonyl]-4-methoxy-2,3-dihydro-1H-indole-2-carboxylic acid Working in a manner similar to preparation II, starting with the product obtained according to preparation XV, the expected compound is obtained in the form of a black solid (yield=89%).

NMR $^1$H (DMSO, 250 MHz) δ: 13.10 (s wide, 1H); 7.76 (d, 2H); 7.57 (d, 2H); 7.19 (t, 1H); 6.99 (d, 1H); 6.66 (d, 1H); 4.99 (dd, 1H); 3.72 (s; 3H); 3.24 (dd, 1H); 2.87 (dd, 1H); 1.25 (s, 9H).

Example 59

1-[[4-(1,1-dimethylethyl)phenyl]sulfonyl]-4-methoxy-N-(2-phenyl ethyl)-2,3-dihydro-1H-)indole-2-carboxamide Working in a manner similar to preparation V, starting with the product obtained according to preparation XVI and benzeneethanamine, the expected compound is obtained in the form of a white solid (yield=72%).

Melting point=188-192° C.

NMR $^1$H (DMSO, 250 MHz) δ: 8.15 (t, 1H); 7.70 (d, 2H); 7.56 (d, 2H); 7.28-7.16 (m, 6H); 7.08 (d, 1H); 6.68 (d, 1H); 4.72 (dd, 1H); 3.72 (s; 3H); 3.35-3.29 (m, 2H); 2.92 (dd, 1H); 2.76-2.65 (m, 3H); 1.25 (s, 9H).

Preparation XVII

1-[[4-(1,1-dimethylethyl)phenyl]sulfonyl]-5-fluoro-2,3-dihydro-1H-indole-2-carboxylic acid, methyl ester Working in a manner similar to preparation XV, starting with 2,3-dihydro-5-fluoro-1H-indole-2-carboxylic acid methyl ester, the expected compound is obtained in the form of a pink solid (yield=72%).

NMR [1]H (DMSO, 300 MHz) δ: 7.74 (d, 2H); 7.58 (d, 2H); 7.40-7.35 (m, 1H); 7.07-7.02 (m, 2H); 5.05 (dd, 1H); 3.72 (s; 3H); 3.26 (dd, 1H); 3.06 (dd, 1H); 1.26 (s, 9H).

Preparation XVIII

1-[[4-(1,1-dimethylethyl)phenyl]sulfonyl]-5-fluoro-2,3-dihydro-1H-indole-2-carboxylic acid Working in a manner similar to preparation II, starting with the product obtained according to preparation XVII, the expected compound is obtained in the form of a red solid (yield=84%).

NMR [1]H (DMSO, 250 MHz) δ: 13.10 (s wide, 1H); 7.74 (d, 2H); 7.56 (d, 2H); 7.38-7.33 (m, 1H); 7.07-7.00 (m, 2H); 4.91 (dd, 1H); 3.28 (dd, 1H); 3.02 (dd, 1H); 1.25 (s, 9H).

Example 60

1-[[4-(1,1-dimethylethyl)phenyl]sulfonyl]-5-fluoro-N-(2-phenylethyl)-2,3-dihydro-1H-indole-2-carboxamide Working in a manner similar to preparation V, starting with the product obtained according to preparation XVIII and benzeneethanamine, the expected compound is obtained in the form of a yellow solid (yield=75

Melting point=168-172° C.

NMR [1]H (DMSO, 300 MHz) δ: 8.19 (t, 1H); 7.66 (d, 2H); 7.56 (d, 2H); 7.47-7.43 (m, 1H); 7.26-6.98 (m, 7H); 4.72 (dd, 1H); 3.37-3.27 (m, 2H); 2.93 (dd, 1H); 2.82 (dd, 1H); 2.72 (t, 2H); 1.25 (s, 9H).

Preparation XIX

1-[[4-(1,1-dimethylethyl)phenyl]sulfonyl]-2,3-dihydro-(2S)-1H-indole-2-carbonyl chloride 14.11 g (111 mmol) of oxalyl chloride are added drop by drop to a solution of 20 g (55.6 mmol) of the acid obtained according to preparation IV in 150 ml of toluene, followed by agitation at ambient temperature. The solvent is evaporated and the product is then recovered in 100 ml of toluene and the solvent is once again eliminated under reduced pressure. The expected product is obtained in the form of a beige solid with a yield of 95%.

Melting point=148° C.

Example 61

4-[2-[[[(2S)-1-[[4-(1,1-dimethylethyl)phenyl]sulfonyl]-2,3-dihydro-1H-indol-2-yl]carbonyl]amino]ethoxy]-N,N-dimethyl-benzenethaneaminium, trifluoroacetate A solution of 132 mg (1.27 mmol) N,N-dimethyl-4-(2-aminoethoxy) benzeneethanamine, bis trifluoroacetate is prepared in 10 ml of dichloromethane, 200 mg (0.529 mmol) of the product obtained according to preparation XIX are added and 402 mg (3.96 mmol) of triethylamine. Agitation takes place for 16 hours at ambient temperature. Water is added to the reaction medium, then extraction takes place with dichloromethane. The organic phase is dried on magnesium sulfate and the solvents are evaporated. The raw product is purified firstly by silica gel chromatography eluting with the help of a toluene/ethanol/ammonia mixture (8/2/0.1; v/v/v), and then secondly by inverse phase chromatography eluting with the help of an acetonitrile/water/trifluoroacetic acid mixture. The expected product is obtained in the form of a colorless oil with a yield of 26%.

NMR [1]H (DMSO, 250 MHz) δ: 9.32 (sl, NH); 8.35 (t, NH); 7.71 (dd, 2H); 7.55 (dd, 2H); 7.45 (d, 1H); 7.30-7.15 (m, 3H); 7.11 (d, 1H); 7.01 (t, 1H); 6.92 (d, 2H); 4.79 (dd, 1H); 3.99 (dd, 2H); 3.6-3.4 (m, 2H); 3.3-3.2 (m, 2H); 3.2-3.0 (m, 1H); 3.0-2.75 (m, 3H); 2.83 (s, 3H); 2.81 (s, 3H); 1.25 (s, 9H).

Preparation XX

4-[2-[[(1,1-dimethylethoxy)carbonyl]amino]ethoxy]-3-fluoro benzoic acid, methyl ester 227 mg (1.32 mmol) of 3-fluoro-4-hydroxybenzoic acid methyl ester, 278 mg (1.72 mmol) of (2-hydroxyethyl)carbamic acid 1,1-dimethyl ester, and 452 mg (2.12 mmol) of triphenylphosphine are mixed in 10 ml of anhydrous toluene. Cooling takes place to −10° C. and then 349 mg (1.72 mmol) of diisopropyl-azodicarboxylate (DIAD) are slowly added. Agitation takes place at −10° C. for 15 minutes and then for 16 hours at ambient temperature. The solvents are evaporated and then the evaporation residue is purified by silica column chromatography eluting with the help of a toluene/ethyl acetate mixture (100/0 for 30 minutes then 80/20; v/v). The expected product is obtained in the form of a white solid with a yield of 93%.

NMR [1]H (DMSO, 250 MHz) δ: 7.78-7.66 (m, 2H); 7.30 (t, 1H); 7.02 (t, 1H); 4.14 (t, 2H); 3.82 (s, 3H); 3.32 (q, 2H); 1.37 (s, 9H).

Preparation XXI 4-(2-aminoethoxy)-3-fluorobenzoic acid, methyl ester 387 mg (1.235 mmol) of the product obtained according to preparation XX are dissolved in 2 ml of dichloromethane and then 1 ml of trifluoroacetic acid are added and agitation takes place for 16 hours at ambient temperature. The solvents are evaporated, ethyl acetate is added and the organic phase is washed with a solution of sodium carbonate at 10%. The organic phase is then dried on magnesium sulfate, filtered and concentrated under reduced pressure. The expected product is obtained in the form of a white solid with a yield of 89%.

NMR [1]H (DMSO, 300 MHz) δ: 7.78 (d, 1H); 7.70 (d, 1H); 7.29 (t, 1H); 4.09 (t, 2H); 3.82 (s, 3H); 2.91 (t, 2H); NH2 not visible Example 62

4-[2-[[[(2S)-1-[[4-(1,1-dimethylethyl)phenyl]sulfonyl]-2,3-dihydro-1H-indol-2-yl]carbonyl]amino]ethoxy]-3-fluorobenzoic acid, methyl ester 230 mg (1.079 mmol) of the product obtained according to preparation XXI are dissolved in 10 ml of anhydrous dichloromethane and then, under argon, 408 mg (1.079 mmol) of 1-[[4-(1,1-dimethylethyl)phenyl]sulfonyl]-2,3-dihydro-(2S)-1H-indole-2-carbonyl chloride and 180.5 μl (1.29 mmol) of triethylamine are added. Agitation takes place for 16 hours at ambient temperature. The dichloromethane is evaporated under reduced pressure, the evaporation residue is recovered in solution in ethyl acetate and the organic phase is washed in water. The organic phase is dried on magnesium sulfate, filtered and evaporated. The evaporation residue is purified by silica column chromatography eluting with the help of a toluene/isopropanol mixture (95/5; v/v). The expected product is obtained in the form of a white solid, with a yield of 46%.

NMR $^1H$ (DMSO, 250 MHz) δ: 8.42 (t, 1H); 7.80-7.67 (m, 4H); 7.54 (d, 2H); 7.44 (d, 1H); 7.32 (t, 1H); 7.20 (t, 1H); 7.10 (d, 1H); 6.99 (t, 1H); 4.78 (dd, 1H); 4.21 (t, 2H); 3.82 (s, 3H); 3.60-3.48 (m, 2H); 3.11 (dd, 1H); 2.90 (dd, 1H); 1.24 (s, 9H).

Example 63

4-[2-[[[(2S)-1-[[4-(1,1-dimethylethyl)phenyl]sulfonyl]-2,3-dihydro-1H-indol-2-yl]carbonyl]amino]ethoxy]-3-fluorobenzoic acid Working in a manner similar to preparation II, starting with the product obtained according to example 62, the expected compound is obtained in the form of a white solid (yield=79%).

NMR $^1H$ (DMSO, 300 MHz) δ: 12.95 (s wide, 1H); 8.43 (t, 1H); 7.76-7.64 (m, 4H); 7.56 (d, 2H); 7.44 (d, 1H); 7.29 (t, 1H); 7.21 (t, 1H); 7.10 (d, 1H); 6.99 (t, 1H); 4.78 (dd, 1H); 4.20 (t, 2H); 3.60-3.47 (m, 2H); 3.11 (dd, 1H); 2.90 (dd, 1H); 1.26 (s, 9H).

Preparation XXII

4-[2-[[(1,1-dimethylethoxy)carbonyl]amino]ethoxy]-3-fluoro benzeneacetic acid, methyl ester Working in a manner similar to preparation XX, starting with 3-fluoro-4-hydroxybenzeneacetic acid methyl ester, the expected compound is obtained in the form of a white solid (yield=92%).

NMR $^1H$ (DMSO, 300 MHz) δ: 7.18-6.98 (m, 4H); 4.01 (t, 2H); 3.62 (s, 2H); 3.60 (s, 3H); 3.29 (q, 2H); 1.37 (s, 9H).

Preparation XXIII 4-(2-aminoethoxy)-3-fluorobenzeneacetic acid, methyl ester

Working in a manner similar to preparation XXI, starting with the product obtained according to preparation XXII, the expected compound is obtained in the form of a colorless oil (yield=91%).

NMR $^1H$ (DMSO, 300 MHz) δ: 7.16-6.99 (m, 3H); 4.35 (s wide, 2H); 4.03 (t, 2H); 3.63 (s, 2H); 3.61 (s, 3H); 2.99 (t, 2H).

Example 64

4-[2-[[[(2S)-1-[[4-(1,1-dimethylethyl)phenyl]sulfonyl]-2,3-dihydro-1H-indol-2-yl]carbonyl]amino]ethoxy]-3-fluoro-benzeneacetic acid, methyl ester Working in a manner similar to example 62, starting with the product obtained according to preparation XXIII, the expected compound is obtained in the form of a beige paste (yield=61%).

NMR $^1H$ (DMSO, 300 MHz) δ: 8.40 (t, 1H); 7.71 (d, 2H); 7.55 (d, 2H); 7.44 (d, 1H); 7.21 (t, 1H); 7.16-6.98 (m, 5H); 4.81 (dd; 1H); 4.08 (t, 2H); 3.63 (s, 2H); 3.61 (s, 3H); 3.58-3.44 (m, 2H); 3.11 (dd, 1H); 2.90 (dd, 1H); 1.25 (s, 9H).

Example 65

4-[2-[[[(2S)-1-[[4-(1,1-dimethylethyl)phenyl]sulfonyl]-2,3-dihydro-1H-indol-2-yl]carbonyl]amino]ethoxy]-3-fluoro-benzeneacetic acid Working in a manner similar to preparation II, starting with the product obtained according to example 64, the expected compound is obtained in the form of a white solid (yield=34%).

NMR $^1H$ (DMSO, 300 MHz) δ: 12.40 (s wide, 1H); 8.40 (t, 1H); 7.71 (d, 2H); 7.55 (d, 2H); 7.44 (d, 1H); 7.21 (t, 1H); 7.16-6.98 (m, 5H); 4.79 (dd; 1H); 4.08 (t, 2H); 3.63-3.40 (m, 4H); 3.11 (dd, 1H); 2.90 (dd, 1H); 1.25 (s, 9H).

Example 66

1-[[4-(1,1-dimethylethyl)phenyl]sulfonyl]-N-[(3-hydroxyphenyl)methyl]-2,3-dihydro-(2S)-1H-indole-2-carboxamide 54 mg (0.53 mmol) of triethylamine are added to a suspension of 42.26 mg (0.265 mmol) of 3-(aminomethyl)phenol hydrochloride in 8 ml of dichloromethane at ambient temperature, then a solution of 100 mg (0.265 mmol) of 1-[[4-(1,1-dimethylethyl)phenyl]sulfonyl]-2,3-dihydro-(2S)-1H-indole-2-carbonyl chloride in 2 ml of dichloromethane is added over 10 minutes. This is left to agitate at ambient temperature for 1 hour. The reaction medium is washed with water, dried on magnesium sulfate, the solvents are evaporated and the evaporation residue is purified by silica column chromatography eluting with the help of a toluene/ethyl acetate mixture (8/2; v/v). The expected product is obtained in the form of a white solid with a yield of 51%.

Melting point=94° C.

Example 67

1-[[4-(1,1-dimethylethyl)phenyl]sulfonyl]-N-[(4-chlorophenyl)methyl]-2,3-dihydro-(2S)-1H-indole-2-carboxamide Working in a manner similar to example 66, starting with 4-chloro-benzenemethanamine hydrochloride, the expected compound is obtained in the form of a white solid (yield=98%).

Melting point=69° C.

Example 68

4-[[[[(2S)-1-[[4-(1,1-dimethylethyl)phenyl]sulfonyl]-2,3-dihydro-1H-indol-2-yl]carbonyl]amino]methyl]benzoic acid, methyl ester Working in a manner similar to example 66, starting with the 4-(aminomethyl)benzoic acid methyl ester hydrochloride, the expected compound is obtained in the form of a white solid (yield=80%).

Melting point=190° C.

Example 69

4-[[[[(2S)-1-[[4-(1,1-dimethylethyl)phenyl]sulfonyl]-2,3-dihydro-1H-indol-2-yl]carbonyl]amino]methyl]benzoic acid Working in a manner similar to preparation II, starting with the product obtained according to example 68, the expected compound is obtained in the form of a white solid (quantitative yield).

Melting point=105-120° C.

Example 70

4-[[[[(2S)-1-[[4-(1,1-dimethylethyl)phenyl]sulfonyl]-2,3-dihydro-1H-indol-2-yl]carbonyl]amino]methyl]benzenepropanoic acid, methyl ester Working in a manner similar to example 66, starting with the (4-aminomethyl)benzenepropanoic acid methyl ester hydrochloride, the expected compound is obtained in the form of a white solid (yield=89%).

Melting point=56° C.

Example 71

4-[[[[(2S)-1-[[4-(1,1-dimethylethyl)phenyl]sulfonyl]-2,3-dihydro-1H-indol-2-yl]carbonyl]amino]methyl] benzenepropanoic acid Working in a manner similar to preparation II, starting with the product obtained according to example 70, the expected compound is obtained in the form of a white solid (yield=97%).

Melting point=80-85° C.

Example 72

4-[[[[(2S)-1-[[4-(1,1-dimethylethyl)phenyl]sulfonyl]-2,3-dihydro-1H-indol-2-yl]carbonyl]amino]methyl] benzeneacetic acid, methyl ester Working in a manner similar to example 67, starting with the (4-aminomethyl)benzeneacetic acid methyl ester hydrochloride, the expected compound is obtained in the form of a colorless oil (yield=89%).

NMR $^1$H (DMSO, 300 MHz) δ: 8.69 (t, NH); 7.72 (d, 2H); 7.56 (d, 2H); 7.46 (d, 1H); 7.3-7.15 (m, 5H); 7.13 (d, 1H); 7.01 (t, 1H); 4.81 (dd, 1H); 4.4-4.2 (m, 2H); 3.65 (s, 2H); 3.60 (s, 3H); 3.13 (dd, 1H); 2.94 (dd, 1H); 1.25 (s, 9H).

Example 73

4-[[[[(2S)-1-[[4-(1,1-dimethylethyl)phenyl]sulfonyl]-2,3-dihydro-1H-indol-2-yl]carbonyl]amino]methyl] benzeneacetic acid Working in a manner similar to preparation II, starting with the product obtained according to example 72, the expected compound is obtained in the form of a white solid (yield=94%).

Melting point=80-85° C.

Preparation XXXIV (2S)-1-[(3,4-dihydro-2,2-dimethyl-2H-1-benzopyran-6-yl)sulfonyl]-2,3-dihydro-1H-indole-2-carboxylic acid, methyl ester Working in a manner similar to preparation I, starting with the (2S)-2,3-dihydro-1H-indole-2-carboxylic acid methyl ester hydrochloride and the 3,4-dihydro-2,2-dimethyl-2H-1-benzopyran-6-yl-sulfonyl chloride, the expected compound is obtained in the form of a yellow oil (yield=93%).

NMR $^1$H (DMSO, 300 MHz) δ: 7.62 (d, 1H); 7.46 (dd, 1H); 7.36 (d, 1H); 7.25-7.13 (m, 2H); 6.99 (t, 1H); 6.78 (d, 1H); 4.99 (dd, 1H); 3.71 (s, 3H); 3.33 (dd, 1H); 3.04 (dd, 1H); 2.83-2.66 (m, 2H); 1.75 (t, 2H); 1.25 (d, 6H).

Preparation XXXV (2S)-1-[(3,4-dihydro-2,2-dimethyl-2H-1-benzopyran-6-yl)sulfonyl]-2,3-dihydro-1H-indole-2-carboxylic acid Working in a manner similar to preparation II, starting with the product obtained according to preparation XXXIV, the expected compound is obtained in the form of a white solid (yield=91%).

NMR $^1$H (DMSO, 300 MHz) δ: 13.05 (s wide, 1H); 7.62 (s, 1H); 7.46 (dd, 1H); 7.34 (d, 1H); 7.23-7.13 (m, 2H); 7.00 (t, 1H); 6.78 (d, 1H); 4.85 (dd, 1H); 3.31 (dd, 1H); 3.00 (dd, 1H); 2.83-2.66 (m, 2H); 1.75 (t, 2H); 1.25 (d, 6H).

Example 74

4-[2-[[[(2S)-1-[(3,4-dihydro-2,2-dimethyl-2H-1-benzopyran-6-yl)sulfonyl]-2,3-dihydro-1H-indol-2-yl]carbonyl]amino]ethoxy]benzoic acid, methyl ester Working in a manner similar to preparation V, starting with the acid obtained according to preparation XXXV and the 4-(2-aminoethoxy)benzoic acid methyl ester, the expected compound is obtained in the form of a white solid (yield=82%).

NMR $^1$H (DMSO, 300 MHz) δ: 8.34 (t, 1H); 7.89 (d, 2H); 7.55 (d, 1H); 7.45-7.36 (m, 2H); 7.20 (t, 1H); 7.11-6.95 (m, 4H); 6.76 (d, 1H); 4.75 (dd, 1H); 4.11 (t, 2H); 3.81 (s, 3H); 3.60-3.34 (m, 2H); 3.06 (dd, 1H); 2.88 (dd, 1H); 2.90-2.63 (m, 2H); 1.74 (t, 2H); 1.25 (d, 6H).

Example 75

4-[2-[[[(2S)-1-[(3,4-dihydro-2,2-dimethyl-2H-1-benzopyran-6-yl)sulfonyl]-2,3-dihydro-1H-indol-2-yl]carbonyl]amino]ethoxy]benzoic acid Working in a manner similar to preparation II, starting with the product obtained according to example 74, the expected compound is obtained in the form of a white solid (yield=32%).

NMR $^1$H (DMSO, 300 MHz) δ: 12.57 (s wide, 1H); 8.34 (t, 1H); 7.87 (d, 2H); 7.55 (d, 1H); 7.45-7.36 (m, 2H); 7.21 (t, 1H); 7.22 (d, 1H); 7.03-6.98 (m, 3H); 6.75 (d, 1H); 4.75 (dd, 1H); 4.10 (t, 2H); 3.60-3.34 (m, 2H); 3.03 (dd, 1H); 2.89 (dd, 1H); 2.84-2.58 (m, 2H); 1.74 (t, 2H); 1.25 (d, 6H).

Preparation XXXVI

3-[3-(aminomethyl)phenoxy]propanoic acid, methyl ester hydrochloride 0.8 g (3.9 mmol) of the 3-(3-cyanophenoxy)propanoic acid methyl ester hydrochloride are dissolved in 20 ml of methanol. 0.4 ml of hydrochloric acid 10 N are added then, under an inert atmosphere, 100 mg of palladium on carbon. The mixture is agitated under a hydrogen atmosphere at ambient temperature and atmospheric pressure. The catalyst is eliminated by filtration, then the filtrate is concentrated under reduced pressure. The residue is recovered using toluene and evaporation is performed again. The product is recrystallised in a methanol/ethyl ether mixture (10/50; v/v), and dried under a vacuum. The expected product is obtained in the form of a white solid with a yield of 84%.

Melting point=134° C.

Example 76

3-[3-[[[[(2S)-1-[[4-(1,1-dimethylethyl)phenyl]sulfonyl]-2,3-dihydro-1H-indol-2-yl]carbonyl]amino] methyl]phenoxy]propanoic acid, methyl ester Working in a manner similar to example 66, starting with the product obtained according to preparation XXXVI, the expected compound is obtained in the form of a white solid (yield=97%).

Melting point=103° C.

Example 77

3-[3-[[[[(2S)-1-[[4-(1,1-dimethylethyl)phenyl]sulfonyl]-2,3-dihydro-1H-indol-2-yl]carbonyl]amino]methyl]phenoxy]propanoic acid Working in a manner similar to preparation II, starting with the product obtained according to example 76, the expected compound is obtained in the form of a white foam (yield=33%).

Melting point=122° C.

NMR $^1$H (DMSO, 250 MHz) δ: 8.69 (t, NH); 7.72 (d, 2H); 7.55 (d, 2H); 7.46 (d, 1H); 7.3-7.1 (m, 3H); 7.02 (t, 1H); 6.9-6.7 (m, 3H); 4.82 (dd, 1H); 4.4-4.2 (m, 2H); 4.12 (t, 2H); 3.13 (dd, 1H); 2.93 (dd, 1H); 2.56 (t, 2H); 1.25 (s, 9H).

Preparation XXXVII (2S)-2,3-dihydro-1-[[4-(1-methylethoxy)phenyl]sulfonyl]-1H-indol-2-carboxylic acid, methyl ester Working in a manner similar to preparation I, starting with the (2S)-2,3-dihydro-1H-indole-2-carboxylic acid methyl ester and the [4-(1-methylethoxy)phenyl]sulfonyl chloride, the expected compound is obtained in the form of a white solid (yield=76%).

NMR $^1$H (DMSO, 300 MHz) δ: 7.73 (d, 2H); 7.36 (d, 1H); 7.22-7.13 (m, 2H); 7.05-6.97 (m, 3H); 4.99 (dd, 1H); 4.69 (hep, 1H); 3.72 (s, 3H); 3.32 (dd, 1H); 3.04 (dd, 1H); 1.24 (d, 6H).

Preparation XXXVIII (2S)-2,3-dihydro-1-[[4-(1-methylethoxy)phenyl]sulfonyl]-1H-indol-2-carboxylic acid Working in a manner similar to preparation II, starting with the product obtained according to preparation XXXVII, the expected compound is obtained in the form of a white solid (yield=98%).

NMR $^1$H (DMSO, 300 MHz) δ: 13.11 (s wide, 1H); 7.72 (d, 2H); 7.35 (d, 1H); 7.22-7.12 (m, 2H); 7.02-6.95 (m, 3H); 4.84 (dd, 1H); 4.68 (hep, 1H); 3.31 (dd, 1H); 3.01 (dd, 1H); 1.24 (d, 6H).

Example 78

4-[2-[[[(2S)-2,3-dihydro-1-[[4-[(1-methylethoxy)phenyl]sulfonyl]-1H-indol-2-yl]carbonyl]amino]ethoxy]benzeneacetic acid 50 mg (0.139 mmol) of acid obtained according to preparation XXXVIII are mixed with 1 ml of dichloromethane. Agitation is performed at 0° C. and 42 μl of triethylamine and 22 μl (0.3 mmol) of thionyl chloride are added. Agitation is performed for 30 minutes at 0° C. The temperature of the reaction medium is allowed to rise to ambient temperature and the solvents are evaporated. A suspension of 30 mg 4-(2-aminoethoxy)benzeneacetic acid in 43 μl of triethylamine and 2 ml of dichloromethane is added to the evaporation residue, and then agitation is performed overnight at ambient temperature. The reaction medium is recovered in 10 ml of dichloromethane, and washing is performed with water. The organic phase is dried on sodium sulfate, filtered and concentrated under reduced pressure. The evaporation residue is purified by silica column chromatography eluting with the help of a dichloromethane/methanol mixture (95/5; v/v). The expected product is obtained in the form of a white solid with a yield of 21%.

NMR $^1$H (DMSO, 250 MHz) δ: 12.25 (s wide, 1H); 8.33 (t, 1H); 7.66 (d, 2H); 7.44 (d, 1H); 7.23-6.86 (m, 9H); 4.79-4.63 (m, 2H); 3.99 (t, 2H); 3.55-3.35 (m, 4H); 3.07 (dd, 1H); 2.90 (dd, 1H); 1.24 (d, 6H)

Preparation XXXIX

7-[[(phenylmethoxy)carbonyl]amino]-1H-indole-2-carboxylic acid, ethyl ester 0.8 g (3.925 mmol) of 7-amino-1H-indole-2-carboxylic acid ethyl ester are mixed with 16 ml of tetrahydrofurane and 1.08 g (7.83 mmol) of potassium carbonate. The reaction medium is cooled to 0° C. and 0.615 ml (4.30 mmol) of benzyl chloroformate are added. Agitation is performed for 1 hour 30 minutes at 0° C., and then the temperature of the mixture is allowed to rise again to ambient temperature over one hour. Then 30 ml of water are added and the product is extracted using ethyl acetate. The combined organic phases are dried on magnesium sulfate, filtered and concentrated under reduced pressure. The evaporation residue is purified by silica column chromatography eluting with the help of a methylcyclohexane/ethyl acetate mixture (90/1; v/v). The expected product is obtained in the form of white crystals with a yield of 61%.

NMR $^1$H (DMSO, 250 MHz) δ: 11.67 (s wide, 1H); 9.68 (s wide, 1H); 7.82 (d, 1H); 7.49-7.34 (m, 6H); 7.16 (s, 1H); 7.05 (t, 1H); 5.21 (s, 2H); 4.35 (q, 2H); 1.34 (t, 3H).

Preparation XL

7-[[(phenylmethoxy)carbonyl]amino]-2,3-dihydro-1H-indole-2-carboxylic acid, methyl ester Working in a manner similar to preparation XIV, starting with the product obtained according to preparation XXXIX, the expected compound is obtained in the form of a brown solid (yield=59%).

NMR $^1$H (DMSO, 250 MHz) δ: 9.07 (s wide, 1H); 7.47-7.31 (m, 5H); 7.28 (d, 1H); 6.81 (d, 1H); 6.59 (t, 1H); 5.78 (d, 1H); 5.14 (s, 2H); 4.48-4.41 (m, 1H); 3.67 (s, 3H); 3.32 (dd, 1H); 3.14 (dd, 1H).

Preparation XLI

1-[[4-(dimethylethyl)phenyl]sulfonyl]-7-[[(phenylmethoxy) carbonyl]amino]-2,3-dihydro-1H-indole-2-carboxylic acid, methyl ester Working in a manner similar to preparation I, starting with the product obtained according to preparation XL, the expected compound is obtained in the form of a yellow paste (yield=71%).

NMR $^1$H (DMSO, 250 MHz) δ: 8.86 (s, 1H); 7.76 (d, 1H); 7.79-7.32 (m, 9H); 7.16 (t, 1H); 6.86 (d, 1H); 5.20-5.15 (m, 3H); 3.64 (s, 3H); 2.86 (d, 1H); 2.36 (dd, 1H); 1.24 (s, 9H).

Preparation XLII

1-[[4-(dimethylethyl)phenyl]sulfonyl]-7-[[(phenylmethoxy)carbonyl]amino]-2,3-dihydro-1H-indole-2-carboxylic acid Working in a manner similar to preparation II, starting with the product obtained according to preparation XLI, the expected compound is obtained in the form of a white solid (yield=84%).

NMR $^1H$ (DMSO, 250 MHz) δ: 13.13 (s wide, 1H); 8.92 (s, 1H); 7.77 (d, 1H); 7.72-7.35 (m, 9H); 7.15 (t, 1H); 6.85 (d, 1H); 5.20 (s, 2H); 5.03 (dd, 1H); 2.83 (d, 1H); 2.28 (dd, 1H); 1.24 (s, 9H).

Preparation XLIII

1-[[4-(dimethylethyl)phenyl]sulfonyl]-N-(2-phenylethyl)-7-[[(phenyl methoxy)carbonyl]amino]-2,3-dihydro-1H-indole-2-carboxamide Working in a manner similar to example 57, starting with the product obtained according to preparation XLII, the expected compound is obtained in the form of a white solid (yield=67%).

NMR $^1H$ (DMSO, 250 MHz) δ: 9.57 (s, 1H); 8.87 (t, 1H); 7.63 (d, 1H); 7.50-7.31 (m, 9H); 7.16 (t, 1H); 7.09-7.06 (m, 3H); 6.97-6.94 (m, 2H); 6.79 (d, 1H); 5.22 (s, 2H); 4.68 (d, 1H); 3.32-3.20 (m, 2H); 2.77 (d, 1H); 2.62 (t, 2H); 2.06 (dd, 1H); 1.25 (s, 9H)

Example 79

7-amino-1-[[4-(dimethylethyl)phenyl]sulfonyl]-N-(2-phenylethyl)-2,3-dihydro-1H-indole-2-carboxamide 30 mg (0.049 mmol) of the product obtained according to preparation XLIII are mixed with 3 ml of methanol. Under a protective atmosphere, 3 mg of palladium on carbon are added and the reaction mixture is agitated under a hydrogen atmosphere at ambient temperature and atmospheric pressure for 5 hours. The reaction medium is filtered, the catalyst is washed with methanol and filtrates are concentrated under reduced pressure. The evaporation residue is purified by silica column chromatography eluting with the help of a methylcyclohexane/ethyl acetate mixture (75/25; v/v). The expected product is obtained in the form of a white solid with a yield of 83%.

NMR $^1H$ (DMSO, 300 MHz) δ: 8.12 (t, 1H); 7.55-7.49 (m, 4H); 7.22-7.03 (m, 5H); 6.84 (t, 1H); 6.59 (d, 1H); 6.22 (d, 1H); 5.49 (s, 2H); 4.67 (d, 1H); 3.31-3.24 (m, 2H); 2.73-2.63 (m, 3H); 2.07 (dd, 1H); 1.25 (s, 9H).

Example 80

4-[2-[[[(2S)-1-[(3,4-dihydro-2,2-dimethyl-2H-1-benzopyran-6-yl)sulfonyl]-2,3-dihydro-1H-indol-2-yl]carbonyl]amino]ethoxy]benzeneacetic acid Working in a manner similar to example 78, starting with the acid obtained according to preparation XXXV and 4-(2-aminoethoxy)benzeneacetic acid, the expected compound is obtained in the form of a yellow solid (yield=74%).

NMR $^1H$ (DMSO, 250 MHz) δ: 12.23 (s wide, 1H); 8.30 (t, 1H); 7.55 (s, 1H); 7.45-7.36 (m, 2H); 7.22-7.09 (m, 4H); 7.00 (t, 1H); 6.87 (m, 2H); 6.76 (d, 1H); 4.76 (dd, 1H); 3.99 (t, 2H); 3.52-3.41 (m, 4H); 3.07-2.62 (m, 4H); 1.75 (t, 2H); 1.25 (d, 6H).

Preparation XLIV

4-[(2-aminoethyl)thio]-3-chloro-benzene acetic acid methyl ester hydrochloride 50 mg (0.144 mmol) of 3-chloro-4-[2-[[(1,1-dimethylethoxy)carbonyl]-amino]-ethylthio]benzeneacetic acid methyl ester are dissolved in 322 μl of trifluoroacetic acid. Agitation is performed for 2 hours at ambient temperature. The trifluoroacetic acid is eliminated by coevaporation with methylcyclohexane. The evaporation residue is dissolved in ethyl acetate and neutralisation takes place by addition of a solution of sodium carbonate at 10%. The organic phase is dried on magnesium sulfate, filtration takes place and concentration under reduced pressure. The expected product is obtained in the form of an orange oil with a quantitative yield.

NMR $^1H$ (DMSO, 250 MHz) δ: 8.24 (s wide, 3H); 7.49-7.43 (m, 2H); 7.27 (d, 1H); 3.71 (s, 2H); 3.62 (s, 3H); 3.32-3.21 (m, 2H); 3.00 (t, 2H).

Example 81

3-chloro-4-[[2-[[[(2S)-1-[[4-(1,1-dimethylethyl)phenyl]sulfonyl]-2,3-dihydro-1H-indol-2-yl]carbonyl]amino]ethyl]thio]benzeneacetic acid, methyl ester 53.6 mg (0,142 mmol) of the product obtained according to preparation XLIV are dissolved in 4 ml of anhydrous dichloromethane, and then 109 mg (3.42 mmol) of resin-based morpholine and 40 mg (0.142 mmol) of [4-(1,1-dimethylethyl)phenyl]sulfonyl chloride are added, agitation takes place for 4 days at ambient temperature. The resin is filtered, the filtrate is concentrated under reduced pressure and the expected product is obtained in the form of a grey solid with a yield of 95%.

NMR $^1H$ (DMSO, 250 MHz) δ: 8.46 (t, 1H); 7.71 (d, 2H); 7.55 (d, 2H); 7.49-7.46 (m, 2H); 7.38 (s, 1H); 7.26-7.20 (m, 2H); 7.12 (d, 1H); 7.01 (t, 1H); 4.73 (dd, 1H); 3.68 (s, 2H); 3.61 (s, 3H); 3.42-3.02 (m, 5H); 2.94 (dd, 1H); 1.25 (s, 9H).

Example 82

3-chloro-4-[[2-[[[(2S)-1-[[4-(1,1-dimethylethyl)phenyl) sulfonyl]-2,3-dihydro-1H-indol-2-yl]carbonyl]amino]ethyl]thio]benzeneacetic acid Working in a manner similar to preparation II, starting with the product obtained according to example 81, the expected compound is obtained in the form of a white solid (yield=60%).

NMR $^1H$ (DMSO, 300 MHz) δ: 12.40 (s wide, 1H); 8.46 (t, 1H); 7.71 (d, 2H); 7.55 (d, 2H); 7.48-7.45 (m, 2H); 7.37 (s, 1H); 7.26-7.20 (m, 2H); 7.12 (d, 1H); 7.01 (t, 1H); 4.73 (dd, 1H); 3.56 (s, 2H); 3.42-3.02 (m, 5H); 2.94 (dd, 1H); 1.25 (s, 9H).

Preparation XLV 3-(4-cyanophenoxy)propanoic acid, methyl ester

A solution of 3.80 g (19.9 mmol) of 3-(4-cyanophenoxy) propanoic acid in 10 ml of methanol is cooled by an ice bath. 3 ml (40 mmol) of thionyl chloride are added drop by drop and then the reaction medium is agitated with solvent reflux for 2 hours. The reaction mixture is then concentrated under reduced pressure and the evaporation residue is purified by silica column chromatography eluting with the help of a dichloromethane/methanol mixture (99/1; v/v). The expected product is obtained in the form of a white solid with a yield of 79%.

Melting point=51° C.

Preparation XLVI

3-[4-(aminomethyl)phenoxy]propanoic acid, methyl ester (hydrochloride)

Working in a manner similar to preparation XXXVI, starting with the product obtained according to preparation XLV, the expected compound is obtained in the form of a white solid (yield=60%).

Melting point=217° C.

Example 83

3-[4-[[[[(2S)-1-[[4-(1,1-dimethylethyl)phenyl]sulfonyl]-2,3-dihydro-1H-indol-2-yl]carbonyl]amino]methyl]phenoxy]propanoic acid, methyl ester Working in a manner similar to example 66, starting with the product obtained according to preparation XLVI, the expected compound is obtained in the form of a white solid (yield=83%).

Melting point=50-52° C.

Example 84

3-[4-[[[[(2S)-1-[[4-(1,1-dimethylethyl)phenyl]sulfonyl]-2,3-dihydro-1H-indol-2-yl]carbonyl]amino]methyl]phenoxy]propanoic acid Working in a manner similar to preparation II, starting with the product obtained according to example 83, the expected compound is obtained in the form of a white solid (yield=41%).

Melting point=75° C.

Example 85

(2S)-1-[[4-(1,1-dimethylethyl)phenyl]sulfonyl]-2,3-dihydro-N-[(4-nitrophenyl)methyl]-1H-indole-2-carboxamide Working in a manner similar to example 66, starting with 4-(aminomethyl)-nitrobenzene, the expected compound is obtained in the form of a white solid (yield=68%).

Melting point=75-80° C.

Example 86

(2S)-1-[[4-(1,1-dimethylethyl)phenyl]sulfonyl]-2,3-dihydro-N-[(4-aminophenyl)methyl]-1H-indole-2-carboxamide Working in a manner similar to preparation XXXVI, starting with the product obtained according to example 85, the expected compound is obtained in the form of a white solid (yield=82%).

Melting point=83-87° C.

Example 87

N-[4-[[[[(2S)-1-[[4-(1,1-dimethylethyl)phenyl]sulfonyl]-2,3-dihydro-1H-indol-2-yl]carbonyl]amino]methyl]phenyl]glycine, methyl ester 400 mg (0.864 mmol) of the product obtained according to example 86, 264 mg (1.728 mmol) of methyl bromoacetate and 120 mg (0.864 mmol) of potassium carbonate in 8 ml of acetone are mixed in a test tube under microwaves. The mixture is heated to 130° C. for one hour with the help of microwaves. The reaction medium is filtered, then the filtrate is concentrated under reduced pressure. The evaporation residue is purified by silica column chromatography eluting with the help of a toluene/ethyl acetate mixture (95/5 then 90/10; v/v). The expected product is obtained in the form of a white solid with a yield of 31%.

Melting point=70° C.

Example 88

N-[4-[[[[(2S)-1-[[4-(1,1-dimethylethyl)phenyl]sulfonyl]-2,3-dihydro-1H-indol-2-yl]carbonyl]amino]methyl]phenyl]glycine Working in a manner similar to preparation II, starting with the product obtained according to example 87, the expected compound is obtained in the form of a yellowish solid (yield=24%).

Melting point=110° C.

Preparation XLVII 2,3-dihydro-2-[[[2-[4-(2-methoxy-2-oxoethyl)phenoxy]ethyl]amino]carbonyl]-(2S)-1H-indole-1-carboxylic acid, 1,1-dimethyl ethyl ester Working in a manner similar to preparation XII, starting with 1-[(1,1-dimethylethoxy)carbonyl]-2,3-dihydro-(2S)-1H-indole-2-carboxylic acid, the expected compound is obtained in the form of a white foam (yield=48

Preparation XLVIII

4-[2-[[[(2S)-2,3-dihydro-1H-indol-2-yl]carbonyl]amino]ethoxy]benzeneacetic acid, methyl ester Working in a manner similar to preparation XXI, starting with the product obtained according to preparation XLVII, the expected compound is obtained in the form of a beige solid (yield=89%).

NMR $^1$H (DMSO, 250 MHz) δ: 8.03 (t, NH); 7.16 (dd, 2H); 7.05-6.80 (m, 4H); 6.65-6.5 (m, 2H); 5.93 (d, NH); 4.22 (ddd, 1H); 3.99 (t, 2H); 3.59 and 3.58 (2s, 5H); 3.55-3.4 (m, 2H); 3.31 (dd, 1H); 2.90 (dd, 1H).

Example 89

4-[2-[[[(2S)-1-[[4-(4-fluorophenoxy)phenyl]sulfonyl]-2,3-dihydro-1H-indol-2-yl]carbonyl]amino]ethoxy]benzeneacetic acid, methyl ester 0.2 g (0.564 mmol) of the product obtained according to preparation XLVIII are dissolved in 4 ml of dichloromethane. 0.086 g (0.846 mmol) of triethylamine and 0.178 g (0.621 mmol) of (4-fluorophenoxy)benzene-sulfonyl chloride are added, and agitation takes place for 20 hours at ambient temperature. The dichloromethane is evaporated, and the evaporation residue is purified by silica column chromatography eluting with the help of a dichloromethane/ethyl acetate mixture (9/1; v/v). The expected product is obtained in the form of a colorless oil with a yield of 76%.

NMR $^1$H (DMSO, 300 MHz) δ: 8.36 (t, NH); 7.77 (d, 2H); 7.43 (d, 1H); 7.35-7.1 (m, 8H); 7.1-6.95 (m, 3H); 6.88 (d, 2H); 4.79 (dd, 1H); 4.00 (t, 2H); 3.60 (s, 5H); 3.65-3.35 (m, 2H); 3.12 (dd, 1H); 2.92 (dd, 1H).

Example 90

4-[2-[[[(2S)-1-[[4-(4-fluorophenoxy)phenyl]sulfonyl]-2,3-dihydro-1H-indol-2-yl]carbonyl]amino]ethoxy]benzeneacetic acid Working in a manner similar to preparation II, starting with the product obtained according to example 89, the expected product is obtained in the form of a white solid with a yield of 65%.

Melting point=65° C.

Preparation IL (2S)-2,3-dihydro-1-[(3,4-dihydro-2,2-dimethyl-2H-1-benzopyran-6-yl)sulfonyl]indole-2-carboxylic acid 1 g (6.13 mmol) of 2,3-dihydro-(2S)-1H-indole-2-carboxylic acid, and 0.97 g (7.05 mmol) of potassium carbonate are solubilised in 2 ml of water. 1.6 g (6.13 mmol) of 3,4-dihydro-2,2-dimethyl-2H-1-benzopyran-6-sulfonyl chloride solubilised in 12 ml of acetonitrile and 2 ml of water are added. Agitation is allowed to take place for 5 hours at ambient temperature. Water is added to the reaction medium, washing is performed with ethyl acetate, the acidity of the aqueous phase is raised to pH 3 by a solution of hydrochloric acid 1 N, and then extraction is performed using ethyl acetate. The organic phases are collected, dried on magnesium sulfate, filtered and concentrated under reduced pressure. The evaporation residue is purified by silica column chromatography eluting with the help of a dichloromethane/methanol (9/1; v/v) mixture. The expected product is obtained in the form of a beige foam with a yield of 73%.

NMR $^1$H (DMSO, 300 MHz) δ: 7.59 (s, 1H); 7.44 (m, 1H); 7.31 (m, 1H); 7.20-7.05 (m, 2H); 6.96 (t, 1H); 6.75 (d, 1H); 7.74 (s wide, 1H); 3.1-2.85 (m, 2H); 2.85-2.60 (m, 2H); 1.73 (t, 2H); 1.25 (m, 6H).

Example 91

(βS)-β-[[[(2S)-1-[(3,4-dihydro-2,2-dimethyl-2H-1-benzopyran-6-yl)sulfonyl]-2,3-dihydro-1H-indol-2-yl]carbonyl]amino]benzene butanoic acid 1,1-dimethyl ethyl ester Working in a manner similar to example 87, starting with the product obtained according to preparation IL and (βS)-β-amino-benzenebutanoic acid t-butyl ester, the expected product is obtained in the form of a white foam with a yield of 15%.

NMR $^1$H (DMSO, 300 MHz) δ: 8.02 (d, 1H); 7.51-7.46 (m, 2H); 7.34 (dd, 1H); 7.25 (t, 1H); 7.16-7.01 (m, 7H); 6.76, (d, 1H); 4.63 (dd, 1H); 4.25 (hex, 1H); 2.94 (dd, 1H); 2.75-2.65 (m, 5H); 2.46-2.30 (m, 2H); 1.75 (t, 2H); 1.39 (s, 9H); 1.26 (m, 6H).

Example 92

(βS)-β-[[[(2S)-1-[(3,4-dihydro-2,2-dimethyl-2H-1-benzopyran-6-yl)sulfonyl]-2,3-dihydro-1H-indol-2-yl]carbonyl]amino]benzene butanoic acid Working in a manner similar to preparation XIII, starting with the product obtained according to example 91, the expected product is obtained in the form of a white foam with a yield of 34%.

NMR $^1$H (DMSO, 300 MHz) δ: 12.30 (s wide, 1H); 8.04 (d, 1H); 7.52 (d, 1H); 7.46 (d, 1H); 7.34 (dd, 1H); 7.24 (t, 1H); 7.18-7.01 (m, 7H); 6.76 (d, 1H); 4.65 (dd, 1H); 4.25 (hex, 1H); 2.96 (dd, 1H); 2.81-2.63 (m, 5H); 2.54-2.30 (m, 2H); 1.75 (t, 2H); 1.26 (m, 6H).

Preparation L (2S)-2,3-dihydro-1-[[4-(phenylmethoxy)phenyl]sulfonyl]indole-2-carboxylic acid, methyl ester Working in a manner similar to preparation IL, starting with the 4-(phenylmethoxy)benzenesulfonyl chloride and 2,3-dihydro-(2S)-1H-indole-2-carboxylic acid methyl ester, the expected product is obtained in the form of a white powder with a yield of 81%.

NMR $^1$H (DMSO, 300 MHz) δ: 7.73 (d, 2H); 7.55 (d, 1H); 7.37-7.33 (m, 5H); 7.20 (t, 1H); 7.07-6.95 (m, 4H); 5.06 (s, 2H); 4.78 (dd, 1H); 3.79 (s, 3H); 3.25-3.05 (m, 2H).

Preparation LI (2S)-2,3-dihydro-1-[(4-hydroxyphenyl)sulfonyl]indole-2-carboxylic acid, methyl ester Working in a manner similar to preparation XLIII, starting with the compound obtained according to preparation L, the expected product is obtained in the form of a beige solid with a yield of 98%.

NMR $^1$H (DMSO, 300 MHz) δ: 10.67 (s wide, 1H); 7.66-7.61 (m, 2H); 7.36-7.33 (m, 1H); 7.22-7.12 (m, 2H); 7.02-6.96 (m, 1H); 6.85-6.81 (m, 2H); 4.97-4.90 (m, 1H); 3.72 (s, 3H); 3.5-3.20 (m, 1H); 3.05-2.95 (m, 1H).

Preparation LII (2S)-2,3-dihydro-1-[[4-(1,1-dimethylethoxy)phenyl]sulfonyl]indole-2-carboxylic acid methyl ester A solution is prepared of 2.4 g (7.2 mmol) of ester obtained according to preparation LI in 140 ml of toluene with heating and 9.6 ml (40 mmol) of N,N-dimethylformamide di-t-butylacetal are slowly added. The reaction mixture is maintained under agitation at 100° C. for 2 hours, then concentrated under reduced pressure. The oily residue is purified by silica gel chromatography eluting with the help of a cyclohexane/ethyl acetate mixture (85/15; v/v). In this way the expected product is obtained in the form of a grey powder with a yield of 38%.

NMR $^1$H ($CDCL_3$, 300 MHz) δ: 7.72 (d, 2H); 7.55 (d, 1H); 7.22 (t, 1H); 7.12-6.95 (m, 4H); 4.81 (dd, 1H); 3.80 (s, 3H) 3.25-3.07 (m, 2H); 1.27 (s, 9H).

Preparation LIII (2S)-2,3-dihydro-1-[[4-(1,1-dimethylethoxy)phenyl]sulfonyl]indole-2-carboxylic acid Working in a manner similar to preparation II, starting with the compound obtained according to preparation LII, the expected product is obtained in the form of a white solid with a yield of 91%.

NMR $^1$H ($CDCL_3$, 300 MHz) δ: 7.65-7.58 (m, 3H); 7.26-7.20 (m, 1H); 7.06-6.95 (m, 4H); 4.77 (dd, 1H); 3.27-3.06 (m, 2H); 1.39 (s, 9H).

Preparation LIV (2S)-2,3-dihydro-1-[[4-(1,1-dimethylethoxy)phenyl]sulfonyl]indole-2-carbonyl chloride Working in a manner similar to preparation XIX, starting with the compound obtained according to preparation LIII, the expected product is obtained with a yield of 98% in the form of a yellow solid that is quickly reacted for the synthesis of example 93.

Example 93

4-[2-[[[(2S)-1-[[4-(1,1-dimethylethoxy)phenyl]sulfonyl]-2,3-dihydro-1H-indol-2-yl]carbonyl]amino]ethoxy]benzeneacetic acid, methyl ester Working in a manner similar to example 61, starting with the compound obtained according to preparation LIV and 4-(2-aminoethoxy)benzeneacetic acid methyl ester, the expected product is obtained in the form of a light yellow solid with a yield of 50%.

NMR $^1H$ (DMSO, 300 MHz) δ: 7.71 (d, 1H); 7.46 (d, 2H); 7.40 (t, 1H); 7.26-7.01 (m, 5H); 7.87 (d, 2H); 7.80 (d, 2H); 4.61 (dd, 1H); 4.01 (m, 2H); 3.80-3.60 (m, 5H); 3.56 (s, 2H); 3.24 (dd, 1H); 2.73 (dd, 1H); 1.36 (s, 9H).

Melting point=45-48° C.

Example 94

4-[2-[[[(2S)-1-[[4-(1,1-dimethylethoxy)phenyl]sulfonyl]-2,3-dihydro-1H-indol-2-yl]carbonyl]amino]ethoxy]benzeneacetic acid Working in a manner similar to preparation II, starting with the compound obtained according to example 93, the expected product is obtained in the form of a white solid with a yield of 68%.

Melting point=68-71° C.

NMR $^1H$ (DMSO, 300 MHz) δ: 12.5 (s wide, 1H); 8.37 (t, 1H); 7.66 (d, 2H); 7.44 (d, 1H); 7.24-6.99 (m, 7H); 6.88 (d, 2H); 4.78 (dd, 1H); 3.99 (dd, 2H); 3.60-3.40 (m, 4H); 3.09-2.85 (m, 2H); 1.34 (s, 9H).

Example 95

Sodium 4-[2-[[[(2S)-1-[[4-(1,1-dimethylethyl)phenyl]sulfonyl]-2,3-dihydro-1H-indol-2-yl]carbonyl]amino]ethoxy]benzeneacetate 960.65 mg (1.791 mmol) of the product obtained in example 55 are dissolved in 1 ml of acetonitrile, and then 3.58 ml (1.791 mmol) of a solution of soda at 0.5 N are added and agitation takes place for 30 minutes at ambient temperature. The reaction medium is lyophilised, the lyophilisate is recrystallised in isopropanol and the desired product is obtained in the form of a white solid with a quantitative yield.

NMR $^1H$ (DMSO, 250 MHz) δ: 8.42 (t, 1H); 7.72 (d, 2H); 7.55 (d, 2H); 7.44 (d, 2H); 7.21 (t, 1H); 7.14-7.10 (m, 3H); 6.99 (t, 1H); 6.80 (d, 1H); 4.81 (dd, 1H); 3.97 (t, 2H); 3.63-3.35 (m, 2H); 3.20 (s, 2H); 3.11 (dd, 1H); 2.90 (dd, 1H); 1.25 (s, 9H).

Biological Activity

Test for Transactivation of GAL4-LXR Chimeras Following Transitory Transfection in COS7 Cells The transactivation tests are based on the capability of the nuclear receptors:

(1) to bond with a specific DNA sequence (RE=Response Element) situated in front of a promoter, via their DNA binding domain (or DBD), and (2) to increase the transcription of a gene under the control of this promoter in the presence of an agonist ligand, via their ligand binding domain (or LBD).

The test for transactivation in COS7 cells developed here aims to evaluate the effect of compounds on the activity of the human LXRs: it allows a validation of the interaction of the compounds with the LXRs and determination of the EC50 of the interaction. This test is based on the use of Gal4-LXR chimera proteins containing the LBD of the LXR (human LXRα or human LXRβ) merged with the DBD of Gal4. The COS7 cells are thus co-transfected in a transitory manner with:

an expression vector coding for the Gal4(DBD)-LXRα (LBD) chimera protein or an expression vector coding for the Gal4(DBD)-LXRβ(LBD) chimera a reporter vector comprising the Gal4-response element recognising the DBD of the Gal4, and situated in front of the minimal promoter PTK that controls the luciferase gene.

The activity of the luciferase produced in this way generates luminescence in the presence of an excess of substrate, a data item that reflects the interaction of the compound with the LBD of the LXR. The compounds of the invention are evaluated in relation to a reference compound (T-0901317, CAS RN: 293754-55-9). According to this test the compounds according to the invention have an EC 50 of less than 1 μM.

The biological properties of the compounds according to the invention demonstrate their potential interest and their utility for their application as active substances in medicinal products intended for the treatment or the prevention of diseases resulting from irregularities in the LXR α and LXR β receptor functions, in particular hypercholesterolemia, dyslipidemia, as well as obesity, diabetes, cardiovascular diseases, certain neurodegenerative diseases and inflammatory diseases. The compounds according to the invention are also of therapeutic interest when it is necessary to correct the parameters indicative of a metabolic syndrome.

Depending on the pathologies to be treated, the compounds of the invention can be used alone or in combination with known treatments for diabetes such as metformine, sulfonylurates, acarbose, PPARγ activators insulin or also in combination with similar compounds of GLP-1 (glucagon-like peptides), DPP-IV, PPARα/γ, PPARδ/γ, PPARδ and panPPAR inhibitors, 11β-HSD1 (11 beta hydroxysteroid dehydrogenase) inhibitors, PTP-1B (protein tyrosin phosphatase) inhibitors, CB1 (cannabinoide) receptor antagonists, glucagon receptor antagonists, PDK (pyruvate dehydrogenase kinase) inhibitors, hepatic glucokinase activators and GSK-3 (glycogen synthase kinase) inhibitors.

The invention also relates to pharmaceutical compositions intended for the treatment or inhibition of the abovementioned diseases when these contain as the active substance at least one of the compounds of formula I according to the invention. These pharmaceutical compositions use conventional formulations comprising pharmaceutically acceptable excipients in order to obtain forms that can preferably be administered orally, such as tablets or gelatine capsules.

In practice, where the compound is administered orally, the daily dosage in humans will preferably be between 5 and 500 mg.

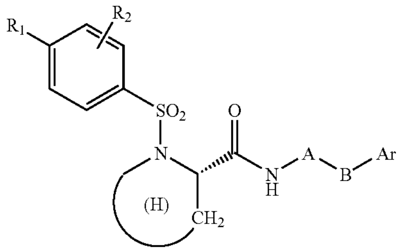
| Ex | (H) | R1 | R2 | A | B | Ar |
|---|---|---|---|---|---|---|
| 1 | Q | $C(CH_3)_3$ | H | $(CH_2)_2$ | — | 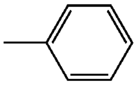 |
| 2 | I | $C(CH_3)_3$ | H | $(CH_2)_2$ | —O— | 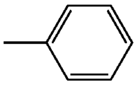 |
| 3 | I | $C(CH_3)_3$ | H | $(CH_2)_2$ | — | 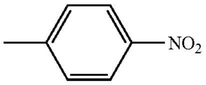 |
| 4 | I | $C(CH_3)_3$ | H | $(CH_2)_2$ | — | 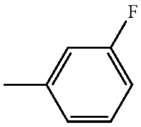 |
| 5 | I | $C(CH_3)_3$ | H | $(CH_2)_2$ | — | 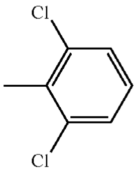 |
| 6 | I | $C(CH_3)_3$ | H | $—CH_2—CH(CH_3)—$ | — | 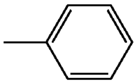 |
| 7 | I | $C(CH_3)_3$ | H | $(CH_2)_2$ | — | 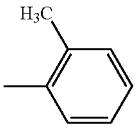 |
| 8 | I | $C(CH_3)_3$ | H | $(CH_2)_2$ | — | 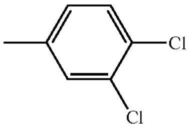 |
| 9 | I | $C(CH_3)_3$ | H | $(CH_2)_2$ | — | 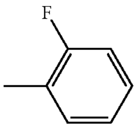 |
| 10 | I | $C(CH_3)_3$ | H | 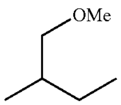 | — | 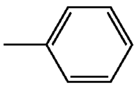 |

-continued
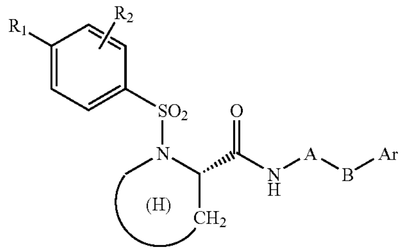
| Ex | (H) | R1 | R2 | A | B | Ar |
|---|---|---|---|---|---|---|
| 11 | I | $C(CH_3)_3$ | H | 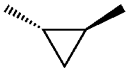 | — | 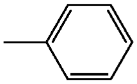 |
| 12 | I | $C(CH_3)_3$ | H | 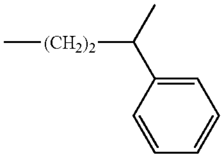 | — | 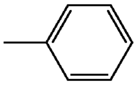 |
| 13 | I | $C(CH_3)_3$ | H | $(CH_2)_2$ | — | 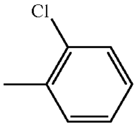 |
| 14 | I | $C(CH_3)_3$ | H | $(CH_2)_2$ | — | 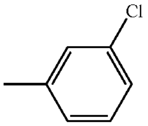 |
| 15 | I | $C(CH_3)_3$ | H | $(CH_2)_2$ | — | 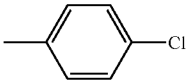 |
| 16 | I | $C(CH_3)_3$ | H | $(CH_2)_2$ | — | 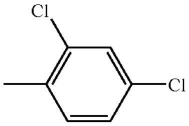 |
| 17 | I | $C(CH_3)_3$ | H | $(CH_2)_3$ | — | 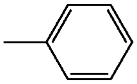 |
| 18 | I | $C(CH_3)_3$ | H | $(CH_2)_4$ | — | 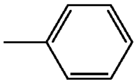 |
| 19 | I | $C(CH_3)_3$ | H | $—CH_2—$ | — | 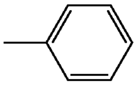 |
| 20 | I | $C(CH_3)_3$ | H | $(CH_2)_2$ | — | 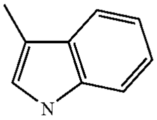 |
| 21 | I | $C(CH_3)_3$ | H | $(CH_2)_2$ | — | 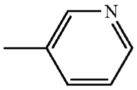 |

-continued
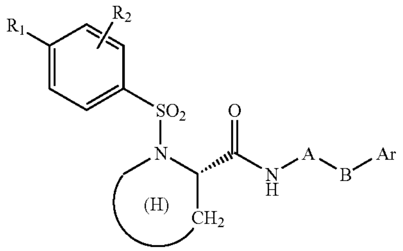
| Ex | (H) | R1 | R2 | A | B | Ar |
|---|---|---|---|---|---|---|
| 22 | I | $C(CH_3)_3$ | H | $—CH_2—$ | —CO— | 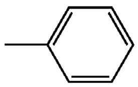 |
| 23 | I | $C(CH_3)_3$ | H | $(CH_2)_2$ | — | 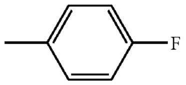 |
| 24 | I | $C(CH_3)_3$ | H | $(CH_2)_2$ | — | 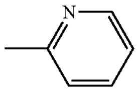 |
| 25 | I | $C(CH_3)_3$ | H | $(CH_2)_2$ | — | 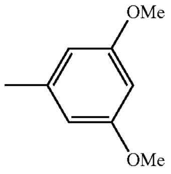 |
| 26 | I | $C(CH_3)_3$ | H | $(CH_2)_2$ | — | 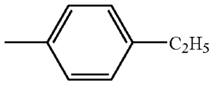 |
| 27 | I | $C(CH_3)_3$ | H | $(CH_2)_2$ | — | 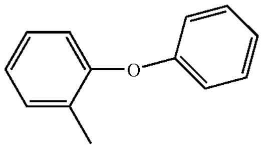 |
| 28 | I | $C(CH_3)_3$ | H | $—CH_2—$ | — | 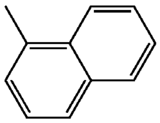 |
| 29 | I | $C(CH_3)_3$ | H | $(CH_2)_2$ | — | 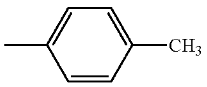 |
| 30 | I | $C(CH_3)_3$ | H | — | — | 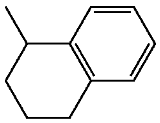 |
| 31 | I | $C(CH_3)_3$ | H | $(CH_2)_2$ | — | 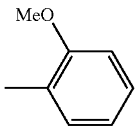 |

-continued
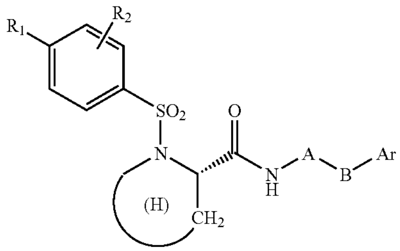
| Ex | (H) | R1 | R2 | A | B | Ar |
|---|---|---|---|---|---|---|
| 32 | I | $C(CH_3)_3$ | H | $(CH_2)_2$ | — | 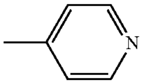 |
| 33 | I | $C(CH_3)_3$ | H | $(CH_2)_2$ | — | 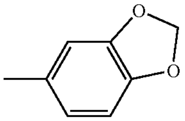 |
| 34 | I | $C(CH_3)_3$ | H | $(CH_2)_2$ | — | 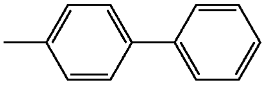 |
| 35 | I | $C(CH_3)_3$ | H | $(CH_2)_2$ | — | 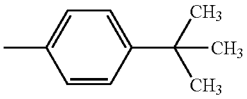 |
| 36 | I | $C(CH_3)_3$ | H | $(CH_2)_2$ | — | 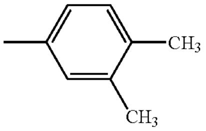 |
| 37 | I | $C(CH_3)_3$ | H | $(CH_2)_2$ | — | 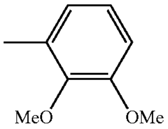 |
| 38 | I | $C(CH_3)_3$ | H | $(CH_2)_2$ | — | 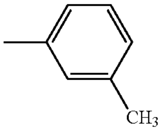 |
| 39 | I | $C(CH_3)_3$ | H | $(CH_2)_2$ | — | 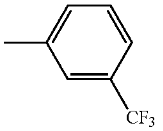 |
| 40 | I | $C(CH_3)_3$ | H | $(CH_2)_2$ | — | 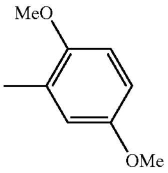 |
| 41 | I | $C(CH_3)_3$ | H | $(CH_2)_2$ | — | 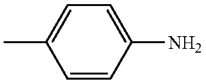 |

-continued
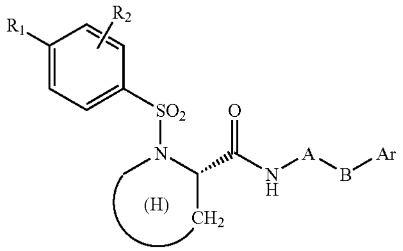
| Ex | (H) | R1 | R2 | A | B | Ar |
|---|---|---|---|---|---|---|
| 42 | I | $C(CH_3)_3$ | H | $(CH_2)_2$ | — | 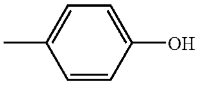 |
| 43 | I | $CH(CH_3)_2$ | H | $(CH_2)_2$ | — | 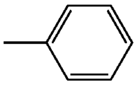 |
| 44 | I | 4-Cl | 3-Cl | $(CH_2)_2$ | — | 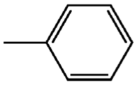 |
| 45 | I | 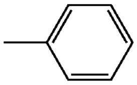 | H | $(CH_2)_2$ | — | 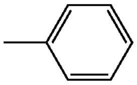 |
| 46 | I | 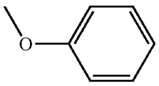 | H | $(CH_2)_2$ | — | 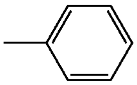 |
| 47# | I | 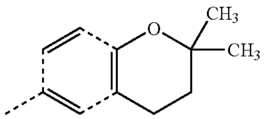 | | $(CH_2)_2$ | — | 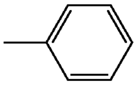 |
| 48# | I | 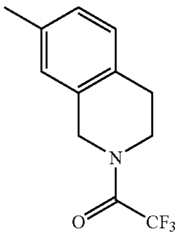 | | $(CH_2)_2$ | — | 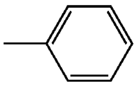 |
| 49 | I | $—O—CH(CH_3)_2$ | H | $(CH_2)_2$ | — | 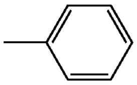 |
| 50 | I | $—C(CH_3)_3$ | H | $(CH_2)_2$ | — | 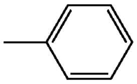 |
| 51 | HI | $—C(CH_3)_3$ | H | $(CH_2)_2$ | — | 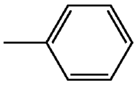 |
| 52 | I | $—C(CH_3)_3$ | H | $(CH_2)_2$ | —O— | 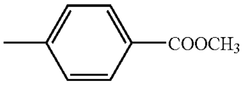 |

-continued
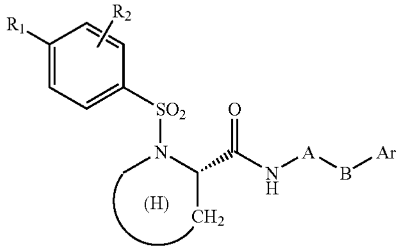
| Ex | (H) | R1 | R2 | A | B | Ar |
|---|---|---|---|---|---|---|
| 53 | I | —$C(CH_3)_3$ | H | $(CH_2)_2$ | —O— | 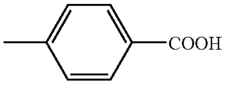 |
| 54 | I | —$C(CH_3)_3$ | H | $(CH_2)_2$ | —O— | 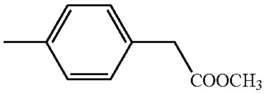 |
| 55 | I | —$C(CH_3)_3$ | H | $(CH_2)_2$ | —O— | 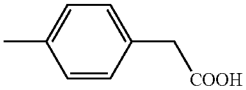 |
| 56 | I | H | 3-FAM* | $(CH_2)_2$ | — | 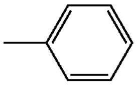 |
| 57 | I | —$C(CH_3)_3$ | H | 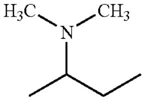 | — | 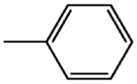 |
| 58 | I | —$C(CH_3)_3$ | H | $(CH_2)_2$ | —O— | 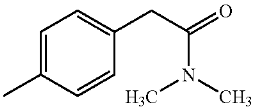 |
| 59** | 4-OMe—I | —$C(CH_3)_3$ | H | $(CH_2)_2$ | — | 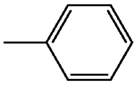 |
| 60** | 5-F—I | —$C(CH_3)_3$ | H | $(CH_2)_2$ | — | 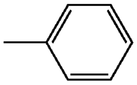 |
| 61 | I | —$C(CH_3)_3$ | H | $(CH_2)_2$ | —O— | 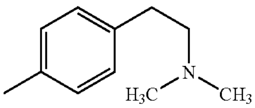 |
| 62 | I | —$C(CH_3)_3$ | H | $(CH_2)_2$ | —O— | 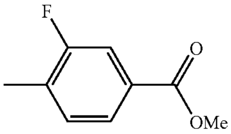 |
| 63 | I | —$C(CH_3)_3$ | H | $(CH_2)_2$ | —O— | 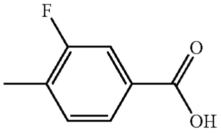 |

-continued
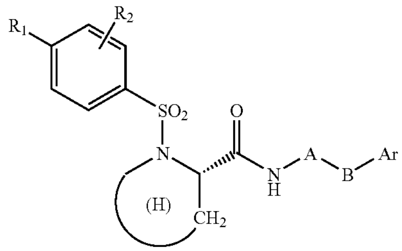
| Ex | (H) | R1 | R2 | A | B | Ar |
|---|---|---|---|---|---|---|
| 64 | I | $—C(CH_3)_3$ | H | $(CH_2)_2$ | —O— | 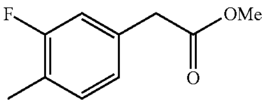 |
| 65 | I | $—C(CH_3)_3$ | H | $(CH_2)_2$ | —O— | 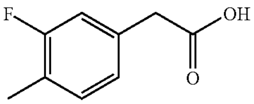 |
| 66 | I | $—C(CH_3)_3$ | H | $CH_2$ | — | 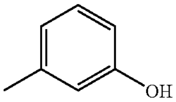 |
| 67 | I | $—C(CH_3)_3$ | H | $CH_2$ | — | 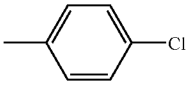 |
| 68 | I | $—C(CH_3)_3$ | H | $CH_2$ | — | 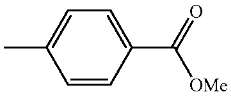 |
| 69 | I | $—C(CH_3)_3$ | H | $CH_2$ | — | 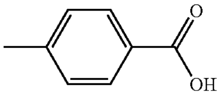 |
| 70 | I | $—C(CH_3)_3$ | H | $CH_2$ | — | 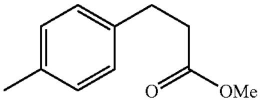 |
| 71 | I | $—C(CH_3)_3$ | H | $CH_2$ | — | 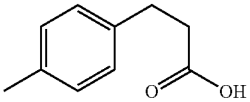 |
| 72 | I | $—C(CH_3)_3$ | H | $CH_2$ | — | 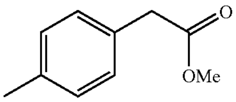 |
| 73 | I | $—C(CH_3)_3$ | H | $CH_2$ | — | 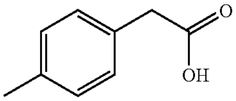 |
| 74# | I | 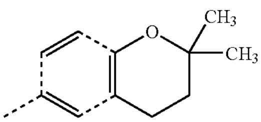 | | $(CH_2)_2$ | —O— | 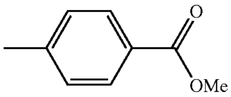 |

-continued
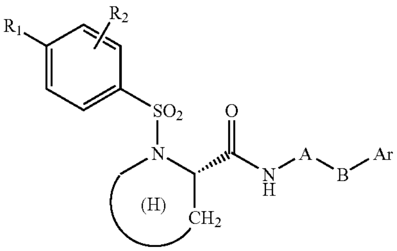
| Ex | (H) | R1 | R2 | A | B | Ar |
|---|---|---|---|---|---|---|
| 75# | I | 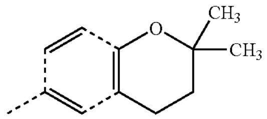 | | $(CH_2)_2$ | —O— | 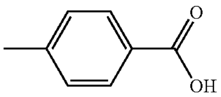 |
| 76 | I | $—C(CH_3)_3$ | H | $CH_2$ | — | 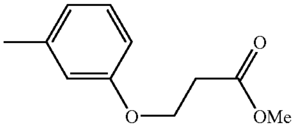 |
| 77 | I | $—C(CH_3)_3$ | H | $CH_2$ | — | 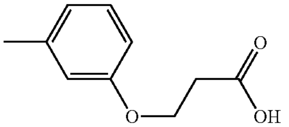 |
| 78 | I | $—O—CH(CH_3)_2$ | H | $(CH_2)_2$ | —O— | 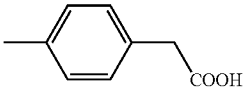 |
| 79** | 7-$NH_2$—I | $—C(CH_3)_3$ | H | $(CH_2)_2$ | — | 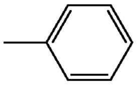 |
| 80# | I | 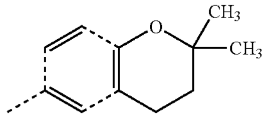 | | $(CH_2)_2$ | —O— | 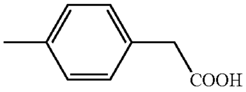 |
| 81 | I | $—C(CH_3)_3$ | | $(CH_2)_2$ | —S— | 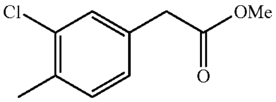 |
| 82 | I | $—C(CH_3)_3$ | H | $(CH_2)_2$ | —S— | 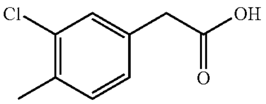 |
| 83 | I | $—C(CH_3)_3$ | H | $CH_2$ | — | 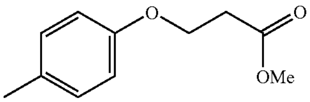 |
| 84 | I | $—C(CH_3)_3$ | H | $CH_2$ | — | 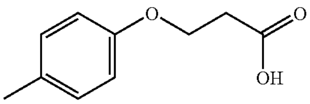 |
| 85 | I | $—C(CH_3)_3$ | H | $CH_2$ | — | 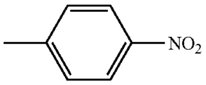 |

-continued
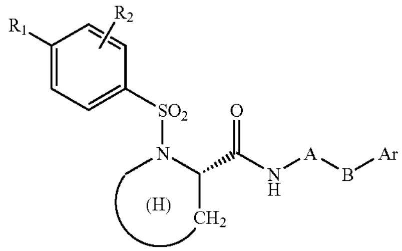
| Ex | (H) | R1 | R2 | A | B | Ar |
|---|---|---|---|---|---|---|
| 86 | I | —$C(CH_3)_3$ | H | $CH_2$ | — | 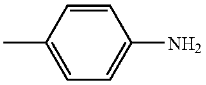 |
| 87 | I | —$C(CH_3)_3$ | H | $CH_2$ | — | 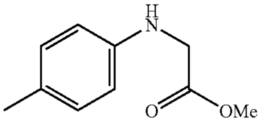 |
| 88 | I | —$C(CH_3)_3$ | H | $CH_2$ | — | 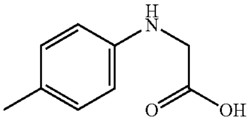 |
| 89 | I | 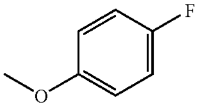 | H | $(CH_2)_2$ | —O— | 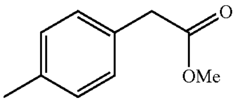 |
| 90 | I | 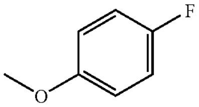 | H | $(CH_2)_2$ | —O— | 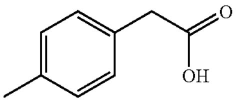 |
| 91# | I | 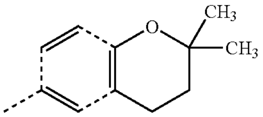 |  | 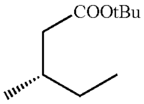 | — | 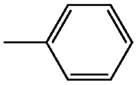 |
| 92# | I | 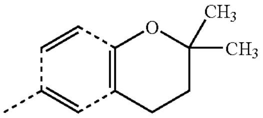 |  | 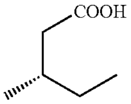 | — | 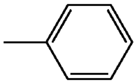 |
| 93 | I | —O—$C(CH_3)_3$ | H | $(CH_2)_2$ | —O— | 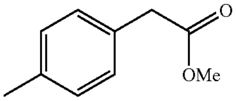 |
| 94 | I | —O—$C(CH_3)_3$ | H | $(CH_2)_2$ | —O— | 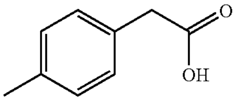 |
| 95 | I | —$C(CH_3)_3$ | H | $(CH_2)_2$ | —O— | 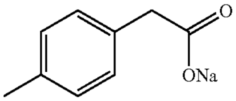 |

Me=$CH_3$

Q=1,2,3,4-tetrahydroquinoline

I=indoline (4-OMe-I=4-methoxy-indolin)

HI=octahydroindole

*3-FAM=3-(trifluoroacetylaminomethyl)

**: racemic compound

#: in this example the formula $R_1$ and $R_2$ represents the unit

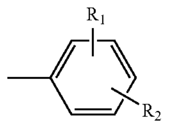

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A benzenesulfonamide compound corresponding to formula I:

I

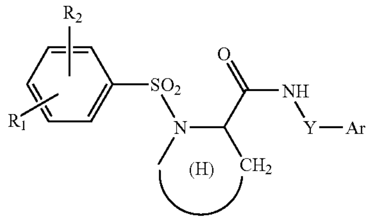

wherein (H) represents a nitrogen-containing 5-membered saturated heterocyclic ring condensed with a phenyl or cyclohexyl ring, optionally substituted by a halogen, a $C_1$-$C_4$ alcoxy group or an $N(R)_2$ group in which R represents the hydrogen atom or a $C_1$-$C_4$ alkyl group, $R_1$ represents:

a chlorine atom, a $C_3$-$C_6$ alkyl group, branched or cyclized, a $C_2$-$C_6$ linear or branched alkoxy group, a phenoxy group, optionally substituted by a halogen, a phenyl group, or an aminomethyl group, optionally substituted by an acetyl or trifluoroacetyl group, $R_2$ represents a hydrogen atom, or, $R_1$ and $R_2$ together form an oxygen-containing or nitrogen-containing heterocycle, optionally substituted by one or more $C_1$-$C_3$ alkyl groups, an acyl group or a $C_2$-$C_3$ perfluoroacyl group, Y represents:

a single bond, a $C_1$-$C_4$, linear or branched or $C_3$-$C_4$ cyclized alkylene group, optionally substituted by a $C_1$-$C_3$ alkoxy group, a phenyl group, an $N(R)_2$ group, or a COOH group, a $-(CH_2)_n-O-$ group, a $-(CH_2)_n-S-$ group, or a $-(CH_2)_m-CO-$ group, n is equal to 2 or 3, m is equal to 1, 2 or 3, R represents the hydrogen atom or a $C_1$-$C_4$ alkyl group Ar represents an aromatic or heteroaromatic ring selected from the group consisting of phenyl, naphthalenyl, tetrahydronaphthalenyl, pyridinyl and indolyl groups, optionally substituted by one or two identical or different $R_3$, $R_4$ substituents selected from the group consisting of halogen, $C_1$-$C_4$ alkyl, $C_1$-$C_4$ alkoxy, nitro, phenyl, phenoxy, trifluoromethyl, amino, hydroxy, and groups of formula $-X-[C(R)_2]_p-COR_5$ in which:

X represents a single bond, an oxygen atom, a sulfur atom or an NH group, $R_5$ represents OR or $N(R)_2$, R represents the hydrogen atom or a $C_1$-$C_4$ alkyl group, and p is equal to 0, 1 or 2;

or $R_3$ and $R_4$ together forming a methylenedioxy group; or a pharmaceutically acceptable salt thereof.

2. A compound according to claim 1, wherein the asymmetric carbon which carries the carboxamide functional group has an S— configuration corresponding to Formula (Ia):

(Ia)

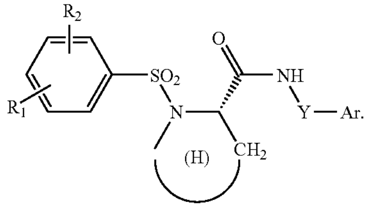

3. A pharmaceutical composition comprising an active compound according to claim 1 and at least one pharmaceutical carrier or adjuvant.

4. A method of treating or inhibiting a disease state selected from the group consisting of atherosclerosis, dyslipidemia, obesity, diabetes, and hypercholesterolemia in a patient in need thereof, said method comprising administering to said patient a pharmaceutically effective amount of a compound according to claim 1.

5. A method according to claim 4, wherein said disease state is hypercholesterolemia.

6. A method according to claim 4, wherein said disease state is diabetes.

7. A process for preparing a compound according to claim 1, said process comprising:

a) reacting an acid of formula:

II

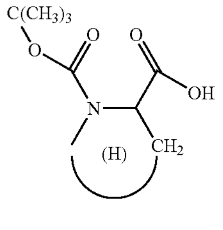

in which (H) represents a nitrogen-containing 5-membered saturated heterocyclic ring condensed with a phenyl or cyclohexyl ring, optionally substituted by a halogen, a $C_1$-$C_4$ alcoxy group or an $N(R)_2$ group in which R represents the hydrogen atom or a $C_1$-$C_4$ alkyl group, with an amine of formula $NH_2$—Y—Ar III in which:

Y represents:

a single bond, a linear, branched or cyclized $C_1$-$C_4$ alkylene group, optionally substituted by a $C_1$-$C_3$ alkoxy group, a phenyl group, an amino group protected by an amino-protecting group other than Boc, or an $N(R)_2$ group in which R represents the hydrogen atom or a $C_1$-$C_4$ alkyl group, a —$(CH_2)_n$—O— group, a —$(CH_2)_n$—S— group, or a —$(CH_2)_m$—CO— group, n is equal to 2 or 3, m is equal to 1, 2 or 3, Ar represents an aromatic or heteroaromatic ring selected from the group consisting of phenyl, naphthalenyl, tetrahydronaphthalenyl, pyridinyl and indolyl groups, optionally substituted by one or two substituents $R_3$, $R_4$ that are identical or different and are selected from the group consisting of halogen, $C_1$-$C_4$ alkyl, $C_1$-$C_4$ alkoxy, nitro, phenyl, phenoxy, trifluoromethyl, hydroxy, amino protected by an amino-protecting group other than Boc, and groups of formula —X—$[C(R)_2]_p$—$COR_5$ in which:

X represents a single bond, an oxygen atom or a sulfur atom, $R_5$ represents OH, OR or $N(R)_2$, R represents a $C_1$-$C_4$ alkyl group, and p is equal to 0, 1 or 2;

or $R_3$ and $R_4$ together form a methylenedioxy group, in an anhydrous solvent and in the presence of a catalyst at a temperature of about ambient temperature and for between 2 and 20 hours in order to obtain an amide of formula IV

IV

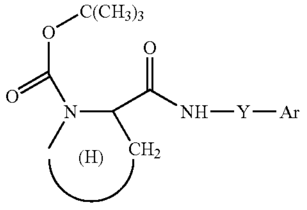

in which (H), Y and Ar retain the meanings given above;

b) reacting the amide of formula IV obtained in step a) with trifluoroacetic acid in a solvent at ambient temperature for between 2 and 20 hours in order to obtain a compound of formula V:

V

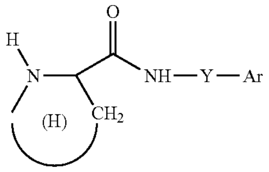

in which (H), Y and Ar retain the meanings given above;

c) reacting the compound of formula V with a benzenesulfonyl chloride of formula VI:

VI

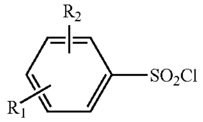

in which $R_1$ represents a chlorine atom, a $C_3$-$C_6$ alkyl group branched or cyclized, a $C_2$-$C_6$ linear or branched alkoxy group, a phenoxy group optionally substituted by a halogen, a phenyl group, or an aminomethyl group optionally substituted by an acetyl or trifluoroacetyl group, and $R_2$ represents a hydrogen atom, or, $R_1$ and $R_2$ together form an oxygenated or nitrogenous heterocycle, optionally substituted by one or more $C_1$-$C_3$ alkyl groups, by an acyl group or by a $C_2$-$C_3$ perfluoroacyl group, in a solvent at ambient temperature for between 2 and 20 hours in order to obtain a compound of formula I

I

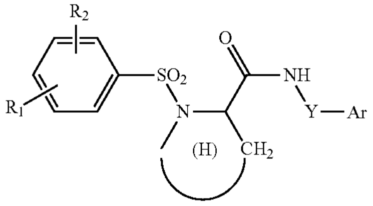

in which $R_1$, $R_2$, (H), Y and Ar retain the meanings given above; and d) if $R_3$ or $R_4$ represents an amino group protected by an amino-protecting group, eliminating the amino-protecting group to obtain a corresponding free amine.

8. A process according to claim 7, wherein said catalyst comprises dicyclohexylcarbodiimide (DCC) or 1-hydroxy-7-azabenzotriazole (HOAT).

9. A process for preparing a compound according to claim 1, said process comprising:

a) reacting a benzenesulfonyl chloride of formula VI

VI

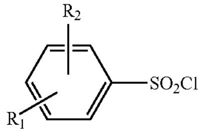

in which $R_1$ represents a chlorine atom, a $C_3$-$C_6$ alkyl group branched or cyclized, a $C_2$-$C_6$ linear or branched alkoxy group, a phenoxy group optionally substituted by a halogen, a phenyl group, or an aminomethyl group substituted by an acetyl or trifluoroacetyl group, and $R_2$ represents a hydrogen atom, or $R_1$ and $R_2$ together form an oxygen-containing or nitrogen-containing heterocycle, optionally substituted by one or more $C_1$-$C_3$ alkyl groups, by an acyl group or by a $C_2$-$C_3$ perfluoroacyl group, with an ester of formula VII:

VII

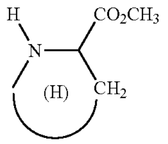

in which (H) represents a nitrogen-containing 5- or 6-membered saturated heterocyclic ring condensed with a phenyl or cyclohexyl ring, optionally substituted by a halogen or a $C_1$-$C_4$ alcoxy group, in an anhydrous solvent, at ambient temperature and for between 2 and 10 hours in order to obtain an ester of formula VIII:

VIII

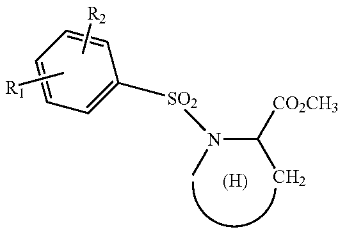

in which (H), $R_1$ and $R_2$ retain the meanings given above, b) converting the ester of formula VIII into acid by treatment with a base in hydroalcoholic medium to obtain an acid of formula IX:

IX

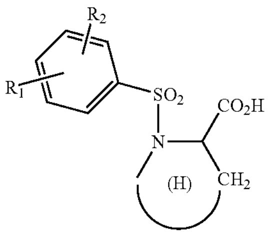

in which (H), $R_1$ and $R_2$ remain unchanged, c) reacting the acid of formula IX with a primary amine of formula III $NH_2$—Y—Ar  III in which Y represents:

a single bond, a $C_1$-$C_4$ alkylene, linear or branched or $C_3$-$C_4$ cyclized group, optionally substituted by a $C_1$-$C_3$ alkoxy group, a phenyl group, an $N(R)_2$ group or a COOH group, a —$(CH_2)_n$—O— group, a —$(CH_2)_n$—S— group, or a —$(CH_2)_m$—CO— group, n is equal to 2 or 3, m is equal to 1, 2 or 3, R represents the hydrogen atom or a $C_1$-$C_4$ alkyl group, Ar represents an aromatic or heteroaromatic ring selected from the group consisting of phenyl, naphthalenyl, tetrahydronaphthalenyl, pyridinyl and indolyl groups, optionally substituted by one or two identical or different $R_3$, $R_4$ substituents selected from the group consisting of halogen, a $C_1$-$C_4$ alkyl, $C_1$-$C_4$ alkoxy, nitro, phenyl, phenoxy, trifluoromethyl, hydroxy, amino protected by an amino-protecting group, and groups of formula —X—$[C(R)_2]_p$—$COR_5$ in which:

X represents a single bond, am oxygen atom or a sulfur atom, $R_5$ represents OH, OR or $N(R)_2$, R represents a $C_1$-$C_3$ alkyl group, and p is equal to 0, 1 or 2;

or $R_3$ and $R_4$ together form a methylenedioxy group, in an anhydrous solvent and in the presence of a catalyst at a temperature of about ambient temperature and for between 2 and 20 hours in order to obtain a compound of formula (I)

I

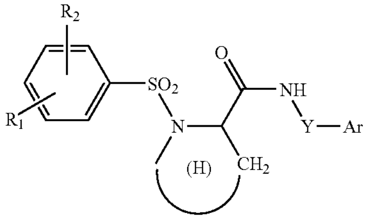

in which (H), $R_1$, $R_2$, Y and Ar retain the meanings given above.

* * * * *